United States Patent
Li et al.

(10) Patent No.: US 10,391,181 B2
(45) Date of Patent: *Aug. 27, 2019

(54) CYCLODEXTRIN AND ANTIBODY-DRUG CONJUGATE FORMULATIONS

(71) Applicant: SEATTLE GENETICS, INC., Bothell, WA (US)

(72) Inventors: Hui Li, Clyde Hill, WA (US); Shan Jiang, Sammamish, WA (US); Mary Wallace, Bothell, WA (US); Damon Meyer, Bellevue, WA (US)

(73) Assignee: Seattle Genetics, Inc., Bothell, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/967,276

(22) Filed: Apr. 30, 2018

(65) Prior Publication Data

US 2018/0369408 A1 Dec. 27, 2018

Related U.S. Application Data

(63) Continuation of application No. 15/454,953, filed on Mar. 9, 2017, now Pat. No. 9,987,374, which is a continuation of application No. 14/774,372, filed as application No. PCT/US2014/024466 on Mar. 12, 2014, now Pat. No. 9,610,361.

(60) Provisional application No. 61/782,231, filed on Mar. 14, 2013, provisional application No. 61/780,185, filed on Mar. 13, 2013.

(51) Int. Cl.

| | |
|---|---|
| *C07K 19/00* | (2006.01) |
| *A61K 9/08* | (2006.01) |
| *A61K 47/18* | (2017.01) |
| *A61K 47/26* | (2006.01) |
| *A61K 47/40* | (2006.01) |
| *A61K 31/5517* | (2006.01) |
| *A61K 47/68* | (2017.01) |
| *C07D 519/00* | (2006.01) |
| *B01D 61/14* | (2006.01) |
| *A61K 47/69* | (2017.01) |
| *A61K 9/19* | (2006.01) |

(52) U.S. Cl.
CPC .......... *A61K 47/6851* (2017.08); *A61K 9/08* (2013.01); *A61K 31/5517* (2013.01); *A61K 47/18* (2013.01); *A61K 47/26* (2013.01); *A61K 47/40* (2013.01); *A61K 47/6803* (2017.08); *A61K 47/6951* (2017.08); *B01D 61/145* (2013.01); *C07D 519/00* (2013.01); *A61K 9/19* (2013.01); *B01D 2315/10* (2013.01); *B01D 2315/16* (2013.01)

(58) Field of Classification Search
CPC .......... C07K 19/00; A61K 9/08; A61K 47/18; A61K 47/26; A61K 47/40; A61K 47/48; A61K 31/5517

See application file for complete search history.

(56) References Cited

U.S. PATENT DOCUMENTS

| | | |
|---|---|---|
| 4,659,696 A | 4/1987 | Hirai et al. |
| 4,727,064 A | 2/1988 | Pitha |
| 6,407,079 B1 | 6/2002 | Muller et al. |
| 8,697,688 B2 | 4/2014 | Howard et al. |
| 8,940,733 B2 | 1/2015 | Howard et al. |
| 9,114,179 B2 | 8/2015 | Zhang et al. |
| 2005/0084536 A1 | 4/2005 | Van Buitenen et al. |
| 2007/0031402 A1 | 2/2007 | Zhang et al. |
| 2012/0028944 A1 | 2/2012 | Loftsson et al. |
| 2012/0238731 A1 | 9/2012 | Fishkin et al. |
| 2013/0028919 A1 | 1/2013 | Howard et al. |
| 2014/0274907 A1 | 9/2014 | Howard et al. |
| 2014/0286970 A1 | 9/2014 | Jeffrey et al. |
| 2014/0302066 A1 | 10/2014 | Jeffrey |

FOREIGN PATENT DOCUMENTS

| | | |
|---|---|---|
| EP | 0335545 B2 | 10/1989 |
| WO | WO1990/003784 A1 | 4/1990 |
| WO | WO2005/065709 A2 | 7/2005 |
| WO | WO2005065717 A2 | 7/2005 |
| WO | WO2007/019232 A2 | 2/2007 |
| WO | WO2010/057107 A1 | 5/2010 |
| WO | WO2010/091150 A1 | 8/2010 |
| WO | WO2011/104625 A1 | 9/2011 |
| WO | WO2011/130613 A1 | 10/2011 |
| WO | WO2012/174555 A2 | 12/2012 |
| WO | WO2014/143622 A1 | 9/2014 |

OTHER PUBLICATIONS

Loftsson, et al., "Cyclodextrin solubilization of benzodiazepines: formulation of midazolam nasal spray," International Journal of Pharmaceutics, Elsevier BV, vol. 212, No. 1, (Jan. 1, 2001), pp. 29-40.

Loftsson, et al., "The Influence of Water-Soluble Polymers and pH on Hydroxypropyl-β-Cyclodextrin Complexation of Drugs", Drug Development and Industrial Pharmacy, 22(5), pp. 401-405, (1996).

Uekama, et al., "Improvement of dissolution and absorption characteristics of benzodiazepines by cyclodextrin complexation," International Journal of Pharmaceutics, Elsevier BV, vol. 16, No. 3, (1983), pp. 327-338.

*Primary Examiner* — Bruck Kifle
(74) *Attorney, Agent, or Firm* — Seattle Genetics, Inc.

(57) ABSTRACT

Disclosed are formulations, including both liquid and lyophilized formulations, comprising a benzodiazepine antibody-drug conjugate (ADC) and a cyclodextrin. Also disclosed are methods of purifying mixtures comprising benzodiazepine antibody-drug conjugates and process drug-related impurities.

1 Claim, 9 Drawing Sheets
Specification includes a Sequence Listing.

SEQUENCE LISTING

<160> NUMBER OF SEQ ID NOS: 23

<210> SEQ ID NO 1
<211> LENGTH: 107
<212> TYPE: PRT
<213> ORGANISM: Artificial
<220> FEATURE:
<223> OTHER INFORMATION: Murine 2H12 VL

<400> SEQUENCE: 1

```
Asp Ile Lys Met Thr Gln Ser Pro Ser Ser Met Tyr Ala Ser Leu Gly
1               5                   10                  15

Glu Arg Val Ile Ile Asn Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Leu
                85                  90                  95

Thr Phe Gly Ala Gly Thr Lys Leu Glu Leu Lys
            100                 105
```

<210> SEQ ID NO 2
<211> LENGTH: 117
<212> TYPE: PRT
<213> ORGANISM: Artificial
<220> FEATURE:
<223> OTHER INFORMATION: Murine 2H12 VH

<400> SEQUENCE: 2

```
Gln Val Gln Leu Gln Gln Ser Gly Pro Glu Leu Val Arg Pro Gly Thr
1               5                   10                  15

Phe Val Lys Ile Ser Cys Lys Ala Ser Gly Tyr Thr Phe Thr Asn Tyr
            20                  25                  30

Asp Ile Asn Trp Val Asn Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Ala Asp Lys Ser Ser Thr Ala Tyr
65                  70                  75                  80

Leu Gln Leu Asn Asn Leu Thr Ser Glu Asn Ser Ala Val Tyr Phe Cys
                85                  90                  95

Ala Ser Gly Tyr Glu Asp Ala Met Asp Tyr Trp Gly Gln Gly Thr Ser
            100                 105                 110

Val Thr Val Ser Ser
        115
```

<210> SEQ ID NO 3
<211> LENGTH: 107
<212> TYPE: PRT
<213> ORGANISM: Artificial
<220> FEATURE:
<223> OTHER INFORMATION: Humanized 2H12 VL

<400> SEQUENCE: 3

Asp Ile Gln Met Thr Gln Ser Pro Ser Leu Ser Ala Ser Val Gly
1               5                   10                  15

Asp Arg Val Thr Ile Asn Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
                35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65              70                  75                  80

Glu Asp Phe Ala Thr Tyr Tyr Cys Leu Gln Tyr Asp Glu Phe Pro Leu
                85                  90                  95

Thr Phe Gly Gly Gly Thr Lys Val Glu Ile Lys
            100                 105

<210> SEQ ID NO 4
<211> LENGTH: 117
<212> TYPE: PRT
<213> ORGANISM: Artificial
<220> FEATURE:
<223> OTHER INFORMATION: Humanized 2H12 VH

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Ile
                35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Ala Asp Thr Ser Ser Thr Ala Tyr
65              70                  75                  80

Met Glu Leu Arg Ser Leu Arg Ser Asp Asp Thr Ala Val Tyr Tyr Cys
                85                  90                  95

Ala Ser Gly Tyr Glu Asp Ala Met Asp Tyr Trp Gly Gln Gly Thr Thr
            100                 105                 110

Val Thr Val Ser Ser
        115

<210> SEQ ID NO 5
<211> LENGTH: 11
<212> TYPE: PRT
<213> ORGANISM: Artificial
<220> FEATURE:
<223> OTHER INFORMATION: 2H12 CDR-L1

<400> SEQUENCE: 5

Lys Ala Ser Gln Asp Ile Asn Ser Tyr Leu Ser
1               5                   10

<210> SEQ ID NO 6
<211> LENGTH: 7
<212> TYPE: PRT
<213> ORGANISM: Artificial
<220> FEATURE:
<223> OTHER INFORMATION: 2H12 CDR-L2

-continued

```
<400> SEQUENCE: 6

Arg Ala Asn Arg Leu Val Asp
1               5

<210> SEQ ID NO 7
<211> LENGTH: 9
<212> TYPE: PRT
<213> ORGANISM: Artificial
<220> FEATURE:
<223> OTHER INFORMATION: 2H12 CDR-L3

<400> SEQUENCE: 7

Leu Gln Tyr Asp Glu Phe Pro Leu Thr
1               5

<210> SEQ ID NO 8
<211> LENGTH: 5
<212> TYPE: PRT
<213> ORGANISM: Artificial
<220> FEATURE:
<223> OTHER INFORMATION: 2H12 CDR-H1

<400> SEQUENCE: 8

Asn Tyr Asp Ile Asn
1               5

<210> SEQ ID NO 9
<211> LENGTH: 17
<212> TYPE: PRT
<213> ORGANISM: Artificial
<220> FEATURE:
<223> OTHER INFORMATION: 2H12 CDR-H2

<400> SEQUENCE: 9

Trp Ile Tyr Pro Gly Asp Gly Ser Thr Lys Tyr Asn Glu Lys Phe Lys
1               5                  10                  15

Ala

<210> SEQ ID NO 10
<211> LENGTH: 8
<212> TYPE: PRT
<213> ORGANISM: Artificial
<220> FEATURE:
<223> OTHER INFORMATION: 2H12 CDR-H3

<400> SEQUENCE: 10

Gly Tyr Glu Asp Ala Met Asp Tyr
1               5

<210> SEQ ID NO 11
<211> LENGTH: 112
<212> TYPE: PRT
<213> ORGANISM: Artificial
<220> FEATURE:
<223> OTHER INFORMATION: Murine 1F6 VH

<400> SEQUENCE: 11

Asp Ile Val Leu Thr Gln Ser Pro Ala Ser Leu Ala Val Ser Leu Gly
1               5                  10                  15

Gln Arg Ala Thr Ile Ser Cys Arg Ala Ser Lys Ser Val Ser Thr Ser
                20                  25                  30

Gly Tyr Ser Phe Met His Trp Tyr Gln Gln Lys Pro Gly Gln Pro Pro
            35                  40                  45
```

```
Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Asp Ala Ala Thr Tyr Tyr Cys Gln His Ser Arg
                85                  90                  95

Glu Val Pro Trp Thr Phe Gly Gly Gly Thr Lys Leu Glu Ile Lys Arg
                100                 105                 110

<210> SEQ ID NO 12
<211> LENGTH: 118
<212> TYPE: PRT
<213> ORGANISM: Artificial
<220> FEATURE:
<223> OTHER INFORMATION: Murine 1F6 VH

<400> SEQUENCE: 12

Gln Ile Gln Leu Val Gln Ser Gly Pro Glu Val Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Thr Tyr Ala Asp Ala Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Tyr Gly Asp Tyr Gly Met Asp Tyr Trp Gly Gln Gly Thr
                100                 105                 110

Ser Val Thr Val Ser Ser
            115

<210> SEQ ID NO 13
<211> LENGTH: 112
<212> TYPE: PRT
<213> ORGANISM: Artificial
<220> FEATURE:
<223> OTHER INFORMATION: Humanized 1F6 VL

<400> SEQUENCE: 13

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
                20                  25                  30

Gly Tyr Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Trp Thr Phe Gly Gln Gly Thr Lys Val Glu Ile Lys Arg
                100                 105                 110
```

```
<210> SEQ ID NO 14
<211> LENGTH: 118
<212> TYPE: PRT
<213> ORGANISM: Artificial
<220> FEATURE:
<223> OTHER INFORMATION: Humanized 1F6 VH

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser
        115

<210> SEQ ID NO 15
<211> LENGTH: 15
<212> TYPE: PRT
<213> ORGANISM: Artificial
<220> FEATURE:
<223> OTHER INFORMATION: 1F6 CDR-L1

<400> SEQUENCE: 15

Arg Ala Ser Lys Ser Val Ser Thr Ser Gly Tyr Ser Phe Met His
1               5                   10                  15

<210> SEQ ID NO 16
<211> LENGTH: 7
<212> TYPE: PRT
<213> ORGANISM: Artificial
<220> FEATURE:
<223> OTHER INFORMATION: 1F6 CDR-L2

<400> SEQUENCE: 16

Leu Ala Ser Asn Leu Glu Ser
1               5

<210> SEQ ID NO 17
<211> LENGTH: 9
<212> TYPE: PRT
<213> ORGANISM: Artificial
<220> FEATURE:
<223> OTHER INFORMATION: 1F6 CDR-L3

<400> SEQUENCE: 17

Gln His Ser Arg Glu Val Pro Trp Thr
1               5

<210> SEQ ID NO 18
<211> LENGTH: 5
<212> TYPE: PRT
<213> ORGANISM: Artificial
<220> FEATURE:
<223> OTHER INFORMATION: 1F6 CDR-H1
```

```
<400> SEQUENCE: 18

Asn Tyr Gly Met Asn
1               5

<210> SEQ ID NO 19
<211> LENGTH: 17
<212> TYPE: PRT
<213> ORGANISM: Artificial
<220> FEATURE:
<223> OTHER INFORMATION: 1F6 CDR-H2

<400> SEQUENCE: 19

Trp Ile Asn Thr Tyr Thr Gly Glu Pro Thr Tyr Ala Asp Ala Phe Lys
1               5                   10                  15

Gly

<210> SEQ ID NO 20
<211> LENGTH: 9
<212> TYPE: PRT
<213> ORGANISM: Artificial
<220> FEATURE:
<223> OTHER INFORMATION: 1F6 CDR-H3

<400> SEQUENCE: 20

Asp Tyr Gly Asp Tyr Gly Met Asp Tyr
1               5

<210> SEQ ID NO 21
<211> LENGTH: 106
<212> TYPE: PRT
<213> ORGANISM: Artificial
<220> FEATURE:
<223> OTHER INFORMATION: Human light chain constant region

<400> SEQUENCE: 21

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 22
<211> LENGTH: 329
<212> TYPE: PRT
<213> ORGANISM: Artificial
<220> FEATURE:
<223> OTHER INFORMATION: Human heavy chain constant region (no C-term K)

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 23
<211> LENGTH: 329
<212> TYPE: PRT
<213> ORGANISM: Artificial
<220> FEATURE:
<223> OTHER INFORMATION: Human heavy chain constant region, S239C (no
    C-term K)

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Ser Leu Gly Thr Gln Thr
 65              70              75              80
Tyr Ile Cys Asn Val Asn His Lys Pro Ser Asn Thr Lys Val Asp Lys
             85              90              95
Lys Val Glu Pro Lys Ser Cys Asp Lys Thr His Thr Cys Pro Pro Cys
            100             105             110
Pro Ala Pro Glu Leu Leu Gly Gly Pro Cys Val Phe Leu Phe Pro Pro
            115             120             125
Lys Pro Lys Asp Thr Leu Met Ile Ser Arg Thr Pro Glu Val Thr Cys
130             135             140
Val Val Val Asp Val Ser His Glu Asp Pro Glu Val Lys Phe Asn Trp
145             150             155             160
Tyr Val Asp Gly Val Glu Val His Asn Ala Lys Thr Lys Pro Arg Glu
            165             170             175
Glu Gln Tyr Asn Ser Thr Tyr Arg Val Val Ser Val Leu Thr Val Leu
            180             185             190
His Gln Asp Trp Leu Asn Gly Lys Glu Tyr Lys Cys Lys Val Ser Asn
            195             200             205
Lys Ala Leu Pro Ala Pro Ile Glu Lys Thr Ile Ser Lys Ala Lys Gly
210             215             220
Gln Pro Arg Glu Pro Gln Val Tyr Thr Leu Pro Pro Ser Arg Asp Glu
225             230             235             240
Leu Thr Lys Asn Gln Val Ser Leu Thr Cys Leu Val Lys Gly Phe Tyr
            245             250             255
Pro Ser Asp Ile Ala Val Glu Trp Glu Ser Asn Gly Gln Pro Glu Asn
            260             265             270
Asn Tyr Lys Thr Thr Pro Pro Val Leu Asp Ser Asp Gly Ser Phe Phe
            275             280             285
Leu Tyr Ser Lys Leu Thr Val Asp Lys Ser Arg Trp Gln Gln Gly Asn
            290             295             300
Val Phe Ser Cys Ser Val Met His Glu Ala Leu His Asn His Tyr Thr
305             310             315             320
Gln Lys Ser Leu Ser Leu Ser Pro Gly
                325
```

CYCLODEXTRIN AND ANTIBODY-DRUG CONJUGATE FORMULATIONS

This application is a continuation of U.S. patent application Ser. No. 15/454,953, filed Mar. 9, 2017, which is a continuation of U.S. patent application Ser. No. 14/774,372 filed Sep. 10, 2015, now U.S. Pat. No. 9,610,361, which is a national stage filing under 35 U.S.C. § 371 of International Application No. PCT/US2014/024466 filed Mar. 12, 2014, which claims the benefit of U.S. Provisional App. No. 61/780,185 filed Mar. 13, 2013 and U.S. Provisional App. No. 61/782,231 filed Mar. 14, 2013, all of which are incorporated by reference in their entirety for all purposes.

BACKGROUND

Antibody-drug conjugates (ADCs) can provide an effective means of delivering a drug to a targeted site in a tissue or organism. Recognition of a target such as a tumor by the antibody minimizes exposure of non-target tissues to toxic chemotherapeutic agents and limits adverse effects associated with the toxicity of "free" drugs (i.e., unbound to a carrier such as an antibody). ADCs can be prepared by a number of techniques. Prior to administration to a human or other subject, the conjugate is purified to remove free drugs and other impurities.

Due to the very high potency of benzodiazepine containing drugs, the removal of drug related impurities from a mixture comprising benzodiazepine ADCs and benzodiazepine drug-related impurities needs to be highly effective. The present invention addresses this and other needs.

GENERAL

Figure 1:
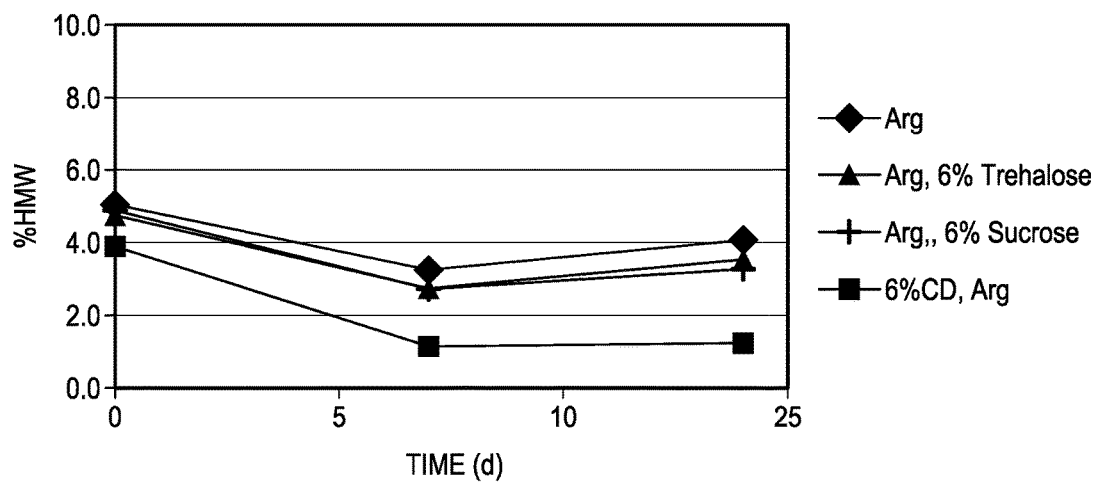
FIG. 1 provides a graph showing the percent high molecular weight (% HMW) species present in various h2H12-1 formulations stored at 25° C. % HMW is determined at time points 0, 7 days, and 14 days.

The present invention is based, in part, on the finding that that removal of benzodiazepine drug-related impurities from a mixture comprising benzodiazepine ADCs and benzodiazepine drug-related impurities (also referred to herein as an ADC mixture) is inefficient due to the nature of benzodiazepine drugs, and the discovery that the addition of cyclodextrin to the mixture enables the efficient clearance of benzodiazepine drug-related impurities. The present inventors have found, inter alia, that the addition of cyclodextrin to a mixture comprising benzodiazepine ADCs and benzodiazepine drug-related impurities prior to performing tangential flow filtration enables the efficient clearance of benzodiazepine drug-related impurities.

The present invention is also based, in part, on the discovery that cyclodextrin-containing formulations of benzodiazepine ADCs exhibit superior stability as compared to formulations not containing cyclodextrin. Improved stability can be demonstrated, for example, by one or more of the following: (i) reduction of the rate and extent of aggregation, (ii) reduction of growth of acidic species and (iii) reduction of the chemical degradation of the drug.

SUMMARY

Provided herein are methods for removing benzodiazepine drug-related impurities from mixtures comprising benzodiazepine ADCS and benzodiazepine drug-related impurities by tangential flow filtration with cyclodextrin. The methods comprise subjecting a mixture comprising benzodizepine ADCs and benzodiazepine drug-related impurities to tangential flow filtration. The use of cyclodextrin during filtration aids in the separation process. Accordingly, provided herein are methods for removing benzodiazepine drug-related impurities from a mixture comprising benzodizepine ADCs and benzodiazepine drug-related impurities comprising comprising subjecting a mixture comprising benzodizepine ADCs and benzodiazepine drug-related impurities to tangential flow filtration wherein cyclodextrin is used to aid in the purification process. In preferred aspects, cyclodextrin is added in an amount sufficient to substantially maintain the solubility of the components in the ADC mixture and prevent aggregation. The cyclodextrin can be, for example, present in the mixture at the start of the tangential flow filtration process or, alternatively, first added to the mixture after initiation of the tangential flow filtration (preferably prior to any substantial removal of impurities). In some aspects, the methods comprise subjecting a mixture comprising benzodizepine ADCs and benzodiazepine drug-related impurities to tangential flow filtration while maintaining a concentration of at least about 1% w/v cylodextrin, at least about 2% w/v cylodextrin, or at least about 3% w/v cyclodextrin in the mixture. The present invention also provides methods comprising providing a mixture comprising benzodizepine ADCs, benzodiazepine drug-related impurities, and cyclodextrin wherein the cyclodextrin is present at a concentration of at least about 1% w/v and subjecting the mixture to tangential flow filtration while maintaining the concentration of at least about 1% w/v cylodextrin in the mixture; methods comprising providing a mixture comprising benzodizepine ADCs, benzodiazepine drug-related impurities, and cyclodextrin wherein the cyclodextrin is present at a concentration of at least about 2% w/v and subjecting the mixture to tangential flow filtration while maintaining the concentration of at least about 2% w/v cylodextrin in the mixture; and methods comprising providing a mixture comprising benzodizepine ADCs, benzodiazepine drug-related impurities, and cyclodextrin wherein the cyclodextrin is present at a concentration of at least about 3% w/v and subjecting the mixture to tangential flow filtration while maintaining the concentration of at least about 3% w/v cylodextrin in the mixture.

The tangential flow filtration can be, for example, constant volume diafiltration or discontinuous diafiltration. The tangential flow filtration device can comprise, for example, a pump, a filtration holder having an inlet, a filtrate outlet, a retentate outlet, an ultrafiltration membrane having a pore size of about 50 Kd or smaller that separates the filtration holder into an upstream compartment and a downstream compartment such that all filtrate must enter the inlet and pass through the ultrafiltration membrane before exiting the filtration holder through the filtrate outlet, a sample reservoir for holding the conjugation reaction mixture, and a buffer reservoir in fluid communication with the sample reservoir. In preferred aspects, the buffer reservoir comprises at least about 1% w/v cyclodextrin, at least about 2% w/v cyclodextrin, or at least about 3% w/v cyclodextrin. The ultrafiltration membrane can have a range of pore sizes including, for example, a pore size of about 30 Kd. The ultrafilatration membrane can be made of many materials, including regenerated cellulose.

The mixture to be purified by tangential flow filtration can be a conjugation reaction mixture, including any of the conjugation reaction mixtures described herein. The benzodiazepine drug-related impurity can be any of the impurities described herein. The benzodizepine drug-related impurity can be quenched or unquenched. For example, the methods can comprise the steps of contacting an antibody or antibody-linker with a benzodizepine drug-linker under conditions sufficient to form a conjugation reaction mixture comprising benzodizepine ADCs. Optionally, the conjugation reaction mixture can be contacted with a quenching agent to form a quenched conjugation reaction mixture. The unquenched or quenched conjugation mixture is subjected to tangential flow filtration as described herein. Alternatively, the methods can comprise the steps of contacting an antibody or antibody-linker with a free drug under conditions sufficient to form a conjugation reaction mixture comprising benzodizepine ADCs. Optionally, the conjugation reaction mixture can be contacted with a quenching agent to form a quenched conjugation reaction mixture. The unquenched or quenched conjugation mixture is subjected to tangential flow filtration as described herein. The benzodizepine drug-related impurity can be, for example, a quenched or unquenched drug-linker or a quenched or unquenched drug. The methods of the present invention are effective at removing benzodizepine drug-related impurities. Preferably, the benzodizepine drug-related impurities are reduced to a level of about 1 µM or less, 0.5 µM or less, 0.1 µM or less, or 0.05 µM or less Beta and gamma cyclodextrins, including chemically modified beta and gamma cyclodextrins, are particularly effective for use in the present invention. The cyclodextrin can be, for example, a hydroxypropyl beta cyclodextrin or sulfobutylether beta cyclodextrin. In some aspects, when the cyclodextrin is a gamma cyclodextrin, the cyclodextrin is maintained at a concentration of at least about 1% w/v during tangential flow filtration and when the cyclodextrin is a beta cyclodextrin, the cyclodextrin is maintained at a concentration of at least about 2% w/v or at least about 3% w/v during tangential flow filtration.

Also provided herein are pharmaceutical formulations comprising a benzodiazepine ADC and cyclodextrin at a concentration of from about 3% w/v to about 30% w/v, preferably a concentration of from about 5% w/v or 6% w/v to about 30% w/v or from about 6% w/v to about 10% w/v. The formulations can be aqueous or non-aqueous form. The formulations can comprise additional excipients such as a lyoprotectant (preferably a sugar, such as, sucrose). They lyoprotectant can be at any concentration effective to act as such, for example, at from about 4% to about 8% (w/v), preferably about 6% (w/v). The pH of the formulation is a physiologically suitable pH. Exemplary pH values are from about 6.0 to about 8.0 or from about 6.5 to 7.5, or from about 7 to 7.5. The formulations typically comprise a buffering agent. The buffering agent can be selected from a wide variety of buffering agents including Tris, acetate, histidine, citrate, phosphate, and succinate. Tris, for example can be present at a concentration of about 20 mM. The concentration of benzodiazepine ADC in the formulation can vary widely. In preferred aspects, the ADC is present at a concentration of from about 0.5 mg/ml to about 30 mg/ml, from about 0.5 mg/ml to about 10 mg/ml, from about 1 mg/ml to about 10 mg/ml, from about 2 mg/ml to about 10 mg/ml, from about 2 mg/ml to about 5 mg/ml, preferably at about 3 mg/ml. Beta and gamma cyclodextrins are particularly effective for use in the formulations, including chemically modified beta and gamma cyclodextrins. The cyclodextrin can be, for example, a hydroxypropyl beta cyclodextrin or sulfobutylether beta cyclodextrin.

Provided herein are pharmaceutical formulations comprising a PBD ADC wherein the concentration of ADC is from about 2 mg/ml to about 5 mg/mol; hydroxypropyl cyclodextrin at a concentration of from about 5% w/v to about 10% w/v; a sugar at a concentration of about 4% to about 8%; and at least one buffering agent; wherein the formulation is in an aqueous solution and the concentration of that at least one buffering agent is effective to maintain a physiologically suitable pH (e.g., about 6 to about 8, more preferably about 7 to about 8 or about 7 to about 7.5).

Provided herein are pharmaceutical formulations comprising a PBD ADC wherein the concentration of ADC is about 3 mg/ml; hydroxypropyl cyclodextrin is at a concentration of about 6%; sucrose is at a concentration of about 6%, Tris at a concentration of about 20 mM, and wherein the pH of the formulation is about 7 to about 7.5 (e.g., about 7.3)

In the methods and formulations provided herein the ADC can have any of the formulas described herein. The ADC can be, for example, a PBD ADC. For example, the ADC can have the formula:

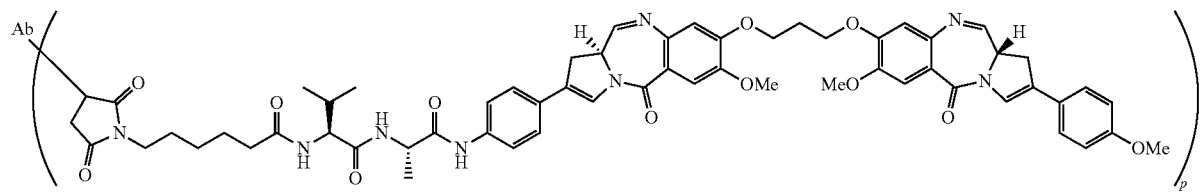

or a pharmaceutically acceptable salt thereof; wherein Ab is a monoclonal antibody and p represents the average number of drug-linker molecules per antibody and is about 2. In other aspects, the ADC can comprise a monoclonal antibody conjugated to an indolinobenzodiazepine dimer, or a monoclonal antibody conjugated to an oxazolidinobenzodiazepine dimer. In the methods and formulation described herein, the antibody can be any antibody, including any monoclonal antibody, including the humanized 2H12 or 1F6 antibodies described herein. Conjugation of the antibody to the drug-linker can be by any of the methods known in the art, including conjugation via a sulfur atom of an introduced cysteine residue Also provided herein are methods for preparing a stabilized, lyophilized antibody-drug conjugate formulation. The methods can comprise providing an aqueous formulation as described herein; and lyophilizing the aqueous solution to form the lyophilized antibody-drug conjugate formulation. Provided herein are also the stabilized, lyophilized antibody-drug conjugate formulations so prepared.

Also provided herein are methods for preventing the chemical degradation and fragmentation of a benzodiapine drug-linker attached to an antibody. The methods can comprise formulating a benzodiapine drug-linker attached to an antibody with at least about 6% w/v gamma cyclodextrin or chemically modified beta cyclodextrin as decribed in any of the embodiments provided herein.

Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The term "heterocycle," as used herein refers to a monocyclic, bicyclic, or polycyclic ring system having from 3 to 14 ring atoms (also referred to as ring members) wherein at least one ring atom in at least one ring is a heteroatom selected from N, O, P, or S (and all combinations and subcombinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocylic heterocycle preferably has 3 to 7 ring members (e.g., 2 to 6 carbon atoms and 1 to 3 heteroatoms independently selected from N, O, P, or S), and a bicyclic heterocycle preferably has 5 to 10 ring members (e.g., 4 to 9 carbon atoms and 1 to 3 heteroatoms independently selected from N, O, P, or S). The ring that includes the heteroatom can be aromatic or non-aromatic.

The term "carbocycle," as used herein refers to a saturated or unsaturated non-aromatic monocyclic, bicyclic, or polycyclic ring system having from 3 to 14 ring atoms (and all combinations and subcombinations of ranges and specific numbers of carbon atoms therein) wherein all of the ring atoms are carbon atoms. Monocyclic carbocycles preferably have 3 to 6 ring atoms, still more preferably 5 or 6 ring atoms. Carbocyles preferably have 3 to 8 carbon ring atoms.

The phrase "pharmaceutically acceptable salt," as used herein, refers to pharmaceutically acceptable organic or inorganic salts of a compound. The compound can contain at least one amino group, and accordingly acid addition salts can be formed with the amino group. Exemplary salts include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

A "polypeptide" or "polypeptide chain" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptide substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "antibody" is used herein to denote immunoglobulin proteins produced by the body in response to the presence of an antigen and that bind to the antigen, as well as antigen-binding fragments and engineered variants thereof. Hence, the term "antibody" includes, for example, intact monoclonal antibodies comprising full-length immunoglobulin heavy and light chains (e.g., antibodies produced using hybridoma technology) and antigen-binding antibody fragments, such as F(ab')$_2$ and Fab fragments. Genetically engineered intact antibodies and fragments, such as chimeric antibodies, humanized antibodies, single-chain Fv fragments, single-chain antibodies, diabodies, minibodies, linear antibodies, multivalent or multispecific (e.g., bispecific) hybrid antibodies, and the like are also included. Thus, the term "antibody" is used expansively to include any protein that comprises an antigen-binding site of an antibody and is capable of specifically binding to its antigen.

The term "genetically engineered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics such as, e.g., complement fixation, interaction with cells, and other effector functions. Typically, changes in the variable region will be made in order to improve the antigen-binding characteristics, improve variable region stability, or reduce the risk of immunogenicity.

An "antigen-binding site of an antibody" is that portion of an antibody that is sufficient to bind to its antigen. The minimum such region is typically a variable domain or a genetically engineered variant thereof. Single-domain binding sites can be generated from camelid antibodies (see Muyldermans and Lauwereys, *J. Mol. Recog.* 12:131-140, 1999; Nguyen et al., *EMBO J.* 19:921-930, 2000) or from VH domains of other species to produce single-domain antibodies ("dAbs"; see Ward et al., *Nature* 341:544-546, 1989; U.S. Pat. No. 6,248,516 to Winter et al.). In certain variations, an antigen-binding site is a polypeptide region having only 2 complementarity determining regions (CDRs) of a naturally or non-naturally (e.g., mutagenized) occurring heavy chain variable domain or light chain variable domain, or combination thereof (see, e.g., Pessi et al., *Nature* 362: 367-369, 1993; Qiu et al., *Nature Biotechnol.* 25:921-929, 2007). More commonly, an antigen-binding site of an antibody comprises both a heavy chain variable (VH) domain and a light chain variable (VL) domain that bind to a common epitope. Within the context of the present invention, an antibody may include one or more components in addition to an antigen-binding site, such as, for example, a second antigen-binding site of an antibody (which may bind to the same or a different epitope or to the same or a different antigen), a peptide linker, an immunoglobulin constant region, an immunoglobulin hinge, an amphipathic helix (see Pack and Pluckthun, *Biochem.* 31:1579-1584, 1992), a non-peptide linker, an oligonucleotide (see Chaudri et al., *FEBS Letters* 450:23-26, 1999), a cytostatic or cytotoxic drug, and the like, and may be a monomeric or multimeric protein. Examples of molecules comprising an antigen-binding site of an antibody are known in the art and include, for example, Fv, single-chain Fv (scFv), Fab, Fab', F(ab')$_2$, F(ab)c, diabodies, dAbs, minibodies, nanobodies, Fab-scFv fusions, bispecific (scFv)$_4$-IgG, and bispecific (scFv)$_2$-Fab. (See, e.g., Hu et al., *Cancer Res.* 56:3055-3061, 1996; Atwell et al., *Molecular Immunology* 33:1301-1312, 1996; Carter and Merchant, *Curr. Opin. Biotechnol.* 8:449-454, 1997; Zuo et al., *Protein Engineering* 13:361-367, 2000; and Lu et al., *J. Immunol. Methods* 267:213-226, 2002.)

As used herein, the term "immunoglobulin" refers to a protein consisting of one or more polypeptides substantially encoded by immunoglobulin gene(s). One form of immunoglobulin constitutes the basic structural unit of native (i.e., natural) antibodies in vertebrates. This form is a tetramer and consists of two identical pairs of immunoglobulin chains, each pair having one light chain and one heavy chain. In each pair, the light and heavy chain variable regions (VL and VH) are together primarily responsible for binding to an antigen, and the constant regions are primarily responsible for the antibody effector functions. Five classes of immunoglobulin protein (IgG, IgA, IgM, IgD, and IgE) have been identified in higher vertebrates. IgG comprises the major class; it normally exists as the second most abundant protein found in plasma. In humans, IgG consists of four subclasses, designated IgG1, IgG2, IgG3, and IgG4. The heavy chain constant regions of the IgG class are identified with the Greek symbol γ. For example, immunoglobulins of the IgG1 subclass contain a γ1 heavy chain constant region. Each immunoglobulin heavy chain possesses a constant region that consists of constant region protein domains (CH1, hinge, CH2, and CH3; IgG3 also contains a CH4 domain) that are essentially invariant for a given subclass in a species. DNA sequences encoding human and non-human immunoglobulin chains are known in the art. (See, e.g., Ellison et al., *DNA* 1:11-18, 1981; Ellison et al., *Nucleic Acids Res.* 10:4071-4079, 1982; Kenten et al., Proc. Natl. Acad. Sci. USA 79:6661-6665, 1982; Seno et al., *Nuc. Acids Res.* 11:719-726, 1983; Riechmann et al., *Nature* 332:323-327, 1988; Amster et al., *Nuc. Acids Res.* 8:2055-2065, 1980; Rusconi and Kohler, *Nature* 314:330-334, 1985; Boss et al., *Nuc. Acids Res.* 12:3791-3806, 1984; Bothwell et al., *Nature* 298:380-382, 1982; van der Loo et al., *Immunogenetics* 42:333-341, 1995; Karlin et al., *J. Mol. Evol.* 22:195-208, 1985; Kindsvogel et al., *DNA* 1:335-343, 1982; Breiner et al., *Gene* 18:165-174, 1982; Kondo et al., *Eur. J. Immunol.* 23:245-249, 1993; and GenBank Accession No. J00228.) For a review of immunoglobulin structure and function, see Putnam, *The Plasma Proteins*, Vol V, Academic Press, Inc., 49-140, 1987; and Padlan, *Mol. Immunol.* 31:169-217, 1994. The term "immunoglobulin" is used herein for its common meaning, denoting an intact antibody, its component chains, or fragments of chains, depending on the context.

Full-length immunoglobulin "light chains" (about 25 Kd or 214 amino acids) are encoded by a variable region gene at the amino-terminus (encoding about 110 amino acids) and a by a kappa or lambda constant region gene at the carboxyl-terminus. Full-length immunoglobulin "heavy chains" (about 50 Kd or 446 amino acids) are encoded by a variable region gene (encoding about 116 amino acids) and a gamma, mu, alpha, delta, or epsilon constant region gene (encoding about 330 amino acids), the latter defining the antibody's isotype as IgG, IgM, IgA, IgD, or IgE, respectively. Within light and heavy chains, the variable and constant regions are joined by a "J" region of about 12 or more amino acids, with the heavy chain also including a "D" region of about 10 more amino acids. (See generally Fundamental Immunology (Paul, ed., Raven Press, N.Y., 2nd ed. 1989), Ch. 7).

An immunoglobulin light or heavy chain variable region (also referred to herein as a "light chain variable domain" ("VL domain") or "heavy chain variable domain" ("VH domain"), respectively) consists of a "framework" region interrupted by three hypervariable regions, also called "complementarity determining regions" or "CDRs." The framework regions serve to align the CDRs for specific binding to an epitope of an antigen. Thus, the term "hypervariable region" or "CDR" refers to the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917, 1987; Chothia et al., *Nature* 342:878-883, 1989. Kabat also provides a widely used numbering convention (Kabat numbering) in which corresponding residues between different heavy chains or between different light chains are assigned the same number. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3.

Unless the context dictates otherwise, the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

The term "chimeric antibody" refers to an antibody having variable domains derived from a first species and constant regions derived from a second species. Chimeric immunoglobulins or antibodies can be constructed, for example by genetic engineering, from immunoglobulin gene segments belonging to different species. The term "humanized antibody," as defined infra, is not intended to encompass chimeric antibodies. Although humanized antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

The term "humanized VH domain" or "humanized VL domain" refers to an immunoglobulin VH or VL domain comprising some or all CDRs entirely or substantially from a non-human donor immunoglobulin (e.g., a mouse or rat) and variable region framework sequences entirely or substantially from human immunoglobulin sequences. The non-human immunoglobulin providing the CDRs is called the "donor" and the human immunoglobulin providing the framework is called the "acceptor." In some instances, humanized antibodies may retain non-human residues within the human variable domain framework regions to enhance proper binding characteristics (e.g., mutations in the frameworks may be required to preserve binding affinity when an antibody is humanized).

A "humanized antibody" is an antibody comprising one or both of a humanized VH domain and a humanized VL domain Immunoglobulin constant region(s) need not be present, but if they are, they are entirely or substantially from human immunoglobulin constant regions.

A CDR in a humanized antibody is "substantially from" a corresponding CDR in a non-human antibody when at least 60%, at least 85%, at least 90%, at least 95% or 100% of corresponding residues (as defined by Kabat) are identical between the respective CDRs. In particular variations of a humanized VH or VL domain in which CDRs are substantially from a non-human immunoglobulin, the CDRs of the humanized VH or VL domain have no more than six (e.g., no more than five, no more than four, no more than three, no more than two, or nor more than one) amino acid substitutions across all three CDRs relative to the corresponding non-human VH or VL CDRs. The variable region framework sequences of an antibody VH or VL domain or, if present, a sequence of an immunoglobulin constant region, are "substantially from" a human VH or VL framework sequence or human constant region, respectively, when at least 85%, at least 90%, at least 95%, or 100% of corresponding residues defined by Kabat are identical. Hence, all parts of a humanized antibody, except possibly the CDRs, are entirely or substantially from corresponding parts of natural human immunoglobulin sequences.

Specific binding of an antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not, however, necessarily imply that a monoclonal antibody binds one and only one target.

With regard to proteins as described herein, reference to amino acid residues corresponding to those specified by SEQ ID NO includes post-translational modifications of such residues.

The term "stabilized," in the context of antibody-drug conjugate formulations as described herein, refers to a formulation in which the antibody-drug conjugate therein essentially retains its physical and chemical identity and integrity upon storage. Various analytical techniques for measuring protein stability are available in the art (see, e.g., *Peptide and Protein Drug Delivery,* 247-301 (Vincent Lee Ed., Marcel Dekker, Inc., New York, N.Y., Pubs. 1991) and Jones, *Adv. Drug Delivery Rev.* 10:29-90, 1993). Exemplary techniques for measuring protein stability are also described herein (see Examples, infra). Stability can be measured at a selected temperature for a selected time period. For rapid testing, the formulation may be kept at a higher or "accelerated" temperature, for example, 40° C. for 1 week to 1 month or more at which time stability is measured. In exemplary embodiments, the formulation is refractory to the formation of by-products of the component antibody protein, for example, high molecular weight aggregation products, low molecular weight degradation or fragmentation products, acidic species, chemical degradants, or mixtures thereof. The term "stability" refers to the length of time over which a molecular species such as an antibody retains its original chemical identity, for example, primary, secondary, and/or tertiary structure.

The term "by-product" includes undesired products, which detract or diminish the proportion of therapeutic antibody-drug conjugate in a given formulation. Typical by-products include aggregates of the antibody-drug conjugate, fragments of the antibody-drug conjugate (for example, produced by degradation of the antibody protein by deamidation or hydrolysis or chemical degradation and fragmentation of the drug-linker), acidic variants of the antibody-drug conjugate, or mixtures thereof.

An antibody-drug conjugate (ADC) is an antibody conjugated to a cytotoxic drug typically via a linker. The linker may comprise a cleavable unit or may be non-cleavable. Cleavable units include, for example, disulfide containing linkers that are cleavable through disulfide exchange, acid-labile linkers that are cleavable at acidic pH, and linkers that are cleavable by hydrolases (e.g., glycosyl hydrolases such as glucuronidases), esterases, and peptidases (e.g., peptide linkers and glucuronide linkers). Non-cleavable linkers are believed to release drug via a proteolytic antibody degradation mechanism.

The term "high molecular weight aggregates" includes aggregates of the antibody-drug conjugate (ADC), as well as aggregates comprising fragments of the ADC (for example, produced by degradation of the polypeptide by, for example, hydrolysis) and aggregates comprising a mixtures of the ADC and such fragments. The presence of high molecular weight aggregates may be determined by, e.g., size-exclusion chromatography (SEC). Typically, high molecular weight aggregates are complexes which have a molecular weight which is greater than the therapeutic monomer ADC. In the case of an ADC in which the antibody component is a tetramer consisting of two identical pairs of immunoglobulin chains, each pair having one light chain and one heavy chain (e.g., of the IgG isotype), such aggregates are greater than about 150 kD. In the case, however, of an ADC in which the antibody component has a molecular weight greater than or less than that of a typical monospecific, tetrameric antibody protein consisting of two immunoglobulin light chains and two immunoglobulin heavy chains (e.g., single-chain antibodies or bispecific antibodies), the size of such aggregates can vary accordingly.

The term "low molecular weight degradation product" includes, for example, fragments of the antibody-drug conjugate (ADC) such as, for example, fragments brought about by deamidation or hydrolysis. The presence of low molecular weight degradation products may be determined by, e.g., size-exclusion chromatography (SEC). Typically, low molecular weight degradation products have a molecular weight that is less than the therapeutic monomer ADC. In the case of an ADC in which the antibody component is a tetramer consisting of two identical pairs of immunoglobulin chains, each pair having one light chain and one heavy chain (e.g., of the IgG isotype), such degradation products are less than about 150 kD. In the case, however, of an ADC in which the antibody component has a molecular weight greater than or less than that of a typical monospecific, tetrameric antibody protein consisting of two immunoglobulin light chains and two immunoglobulin heavy chains (e.g., single-chain antibodies or bispecific antibodies), the size of such degradation products can vary accordingly.

An "acidic variant" of an antibody-drug conjugate (ADC) of interest is an ADC variant that is more acidic than the experimental PI of the ADC. The presence of acid variants may be determined by, e.g., cation exchange chromatography or imaging capillary IEF (icIEF). An example of an acidic variant is a deamidated variant. Deamidated variants of a protein molecule are those in which one or more neutral amide side chain(s) have been converted to a residue with an overall acidic character (e.g., one or more asparagine residue(s) of the original polypeptide have been converted to aspartate).

The term "diluent" as used herein refers to a solution suitable for altering or achieving an exemplary or appropriate concentration or concentrations as described herein.

The term "container" refers to something into which an object or liquid can be placed or contained, e.g., for storage (for example, a holder, receptacle, vessel, or the like).

The term "administration route" includes art-recognized administration routes for delivering a therapeutic protein such as, for example, parenterally, intravenously, intramuscularly, or subcutaneously. For administration of an ADC for the treatment of cancer, administration into the systemic circulation by intravenous or subcutaneous administration may be desired. For treatment of a cancer characterized by a solid tumor, administration can be localized directly into the tumor, if so desired.

The term "treatment" refers to the administration of a therapeutic agent to a patient, who has a disease with the purpose to cure, heal, alleviate, delay, relieve, alter, remedy, ameliorate, improve or affect the disease.

The term "patient" includes human and other mammalian subjects that receive either prophylactic or therapeutic treatment.

The term "effective amount," "effective dose," or "effective dosage" refers to an amount that is sufficient to achieve or at least partially achieve the desired effect, e.g., sufficient to inhibit the occurrence or ameliorate one or more symptoms of a disease or disorder. An effective amount of a pharmaceutical composition is administered in an "effective regime." The term "effective regime" refers to a combination of amount of the composition being administered and dosage frequency adequate to accomplish prophylactic or therapeutic treatment of the disease or disorder.

The term "dosage unit form" (or "unit dosage form") as used herein refers to a physically discrete unit suitable as unitary dosages for a patient to be treated, each unit containing a predetermined quantity of active compound (an ADC in accordance with the present invention) calculated to produce the desired therapeutic effect in association with the required pharmaceutical carrier, diluent, or excipient. The specification for the dosage unit forms of the invention are dictated by and directly dependent on the unique characteristics of the active compound and the particular therapeutic effect to be achieved, and the limitations inherent in the art of compounding such an active compound for the treatment of patients.

Actual dosage levels of an an ADC in a formulation of the present invention may be varied so as to obtain an amount of the ADC that is effective to achieve a desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well-known in the medical arts.

A "cytotoxic effect" refers to the depletion, elimination and/or the killing of a target cell. A "cytotoxic agent" refers to an agent that has a cytotoxic effect on a cell.

A "cytostatic effect" refers to the inhibition of cell proliferation. A "cytostatic agent" refers to an agent that has a cytostatic effect on a cell, thereby inhibiting the growth and/or expansion of a specific subset of cells.

Two amino acid sequences have "100% amino acid sequence identity" if the amino acid residues of the two amino acid sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art. (See, e.g., Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in *Methods in Gene Biotechnology* 123-151 (CRC Press, Inc. 1997); Bishop (ed.), *Guide to Human Genome Computing* (2nd ed., Academic Press, Inc. 1998).) Two amino acid sequences are considered to have "substantial sequence identity" if the two sequences have at least 80%, at least 85%, at least 90%, or at least 95% sequence identity relative to each other.

Percentage sequence identities are determined with antibody sequences maximally aligned by the Kabat numbering convention. After alignment, if a subject antibody region (e.g., the entire variable domain of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

The term "pharmaceutical formulation" refers to a preparation which is in such form as to permit the biological activity of the active ingredient to be effective (when administered to a subject), and which contains no additional components which are unacceptably toxic to a subject to which the formulation would be administered. Such formulations are sterile.

Compositions or methods "comprising" one or more recited elements may include other elements not specifically recited.

Reference to a numerical range herein (e.g., "X to Y" or "from X to Y") includes the endpoints defining the range and all values falling within the range.

Unless otherwise apparent from the context, when a value is expressed as "about" X or "approximately" X, the stated value of X will be understood to be accurate to ±10%.

DESCRIPTION OF ILLUSTRATIVE EMBODIMENTS

Benzodiazepine Antibody-Drug Conjugates

A benzodiazepine antibody-drug conjugate refers to an antibody conjugated to a benzodiazepine dimer typically, although not necessarily, via a linker. A benzodiazepine drug-linker refers to a benzodiazepine dimer attached to a linker. The linker component of the benzodiazepine drug-linker will typically have a reactive group for attachment to the antibody. A benzodiazepine compound has at its core a benzene ring fused to a diazepine ring. Exemplary ring structures for the benzene ring fused to a diazepine ring are as follows: 3,4-dihydro-1H-benzo[e][1,4]diazepin-5(2H)-one 3H-benzo[e][1,4]diazepin-5(4H)-one

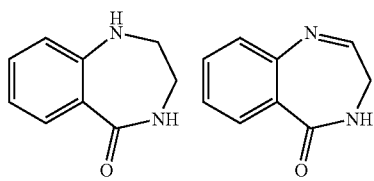

Benzodiazepine compounds differ in the number, type and position of substituents on both rings and in the degree of saturation of the diazepine ring. They also differ in the number of additional rings fused to the benzene and/or diazepine ring. Included within the definition of benzodiazepine compounds are those in which the benzene or diazepine ring is fused to one or more aromatic or non-aromatic carbocyclic or heterocyclic rings. A benzodiazepine dimer is a compound that has been formed by joining two benzodiazepine units together, via a tether.

The antibody component of the benzodiazepine antibody-drug conjugate can be conjugated to one or more benzodiazepine drug-linkers e.g., 1 to 20 drug-linkers. In some aspects, the antibody component of the benzodiazepine antibody-drug conjugate will be conjugated to 1, 2, 3, or 4 drug-linkers. Conjugation can be via different positions on the antibody. In some aspects, conjugation will be via a sulfur atom of a cyteine residue. In some aspects the cysteine residue is a cysteine residue of the interchain disulfides of the antibody. In other aspects, the cysteine residue is engineered into the antibody. In some aspects, the cysteine residue is engineered into the antibody at position 239 (human IgG1) as determined by the EU index (Kabat, *Sequences of Proteins of Immunological Interest* (National Institutes of Health, Bethesda, Md., 1987 and 1991)). In some aspects, there will be an average 2 drug-linkers per antibody in a benzodiazepine ADC mixture or formulation. and the drug-linkers will be conjugated to a cysteine residue introduced into the antibody at position 239 (human IgG1) as determined by the EU index (Kabat, *Sequences of Proteins of Immunological Interest* (National Institutes of Health, Bethesda, Md., 1987 and 1991)).

In one aspect, the benzodiazepine dimer is a pyrrolobenzodiazepine (PBD) dimer. PBDs are of the general structure:

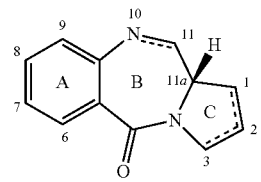

PBDs differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine ether (NH—CH(OR)) at the N10-C11 position, which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site. The ability of PBDs to form an adduct in the minor groove enables them to interfere with DNA processing, hence their use as antitumour agents. The biological activity of these molecules can be potentiated by, for example, joining two PBD units together (e.g., through C8/C'-hydroxyl functionalities via a flexible alkylene linker). The PBD dimers are thought to form sequence-selective DNA lesions such as the palindromic 5'-Pu-GATC-Py-3' interstrand cross-link which is thought to be mainly responsible for their biological activity.

Exemplary PBD dimers to be used as conjugates are as follows:

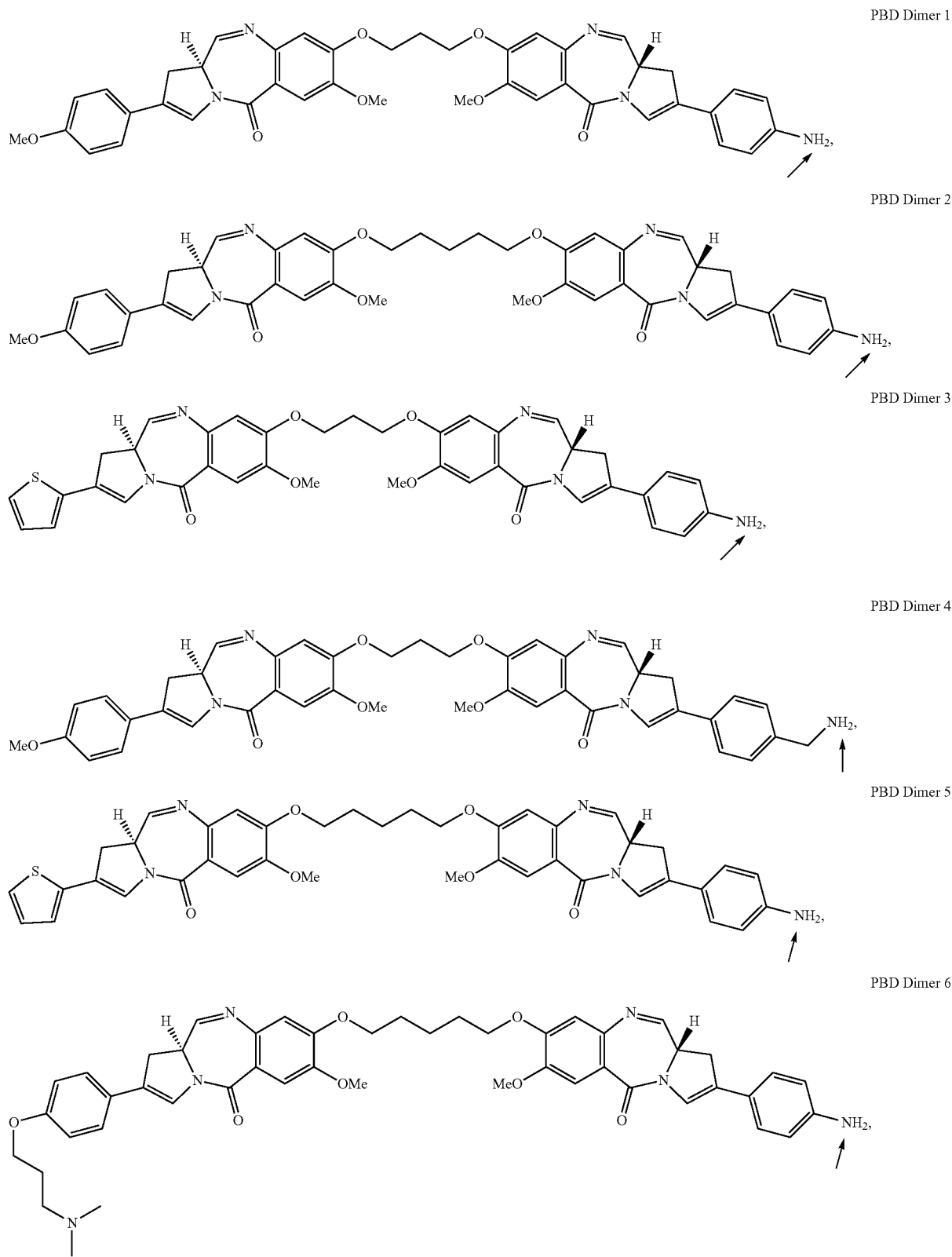

PBD Dimer 1

PBD Dimer 2

PBD Dimer 3

PBD Dimer 4

PBD Dimer 5

PBD Dimer 6

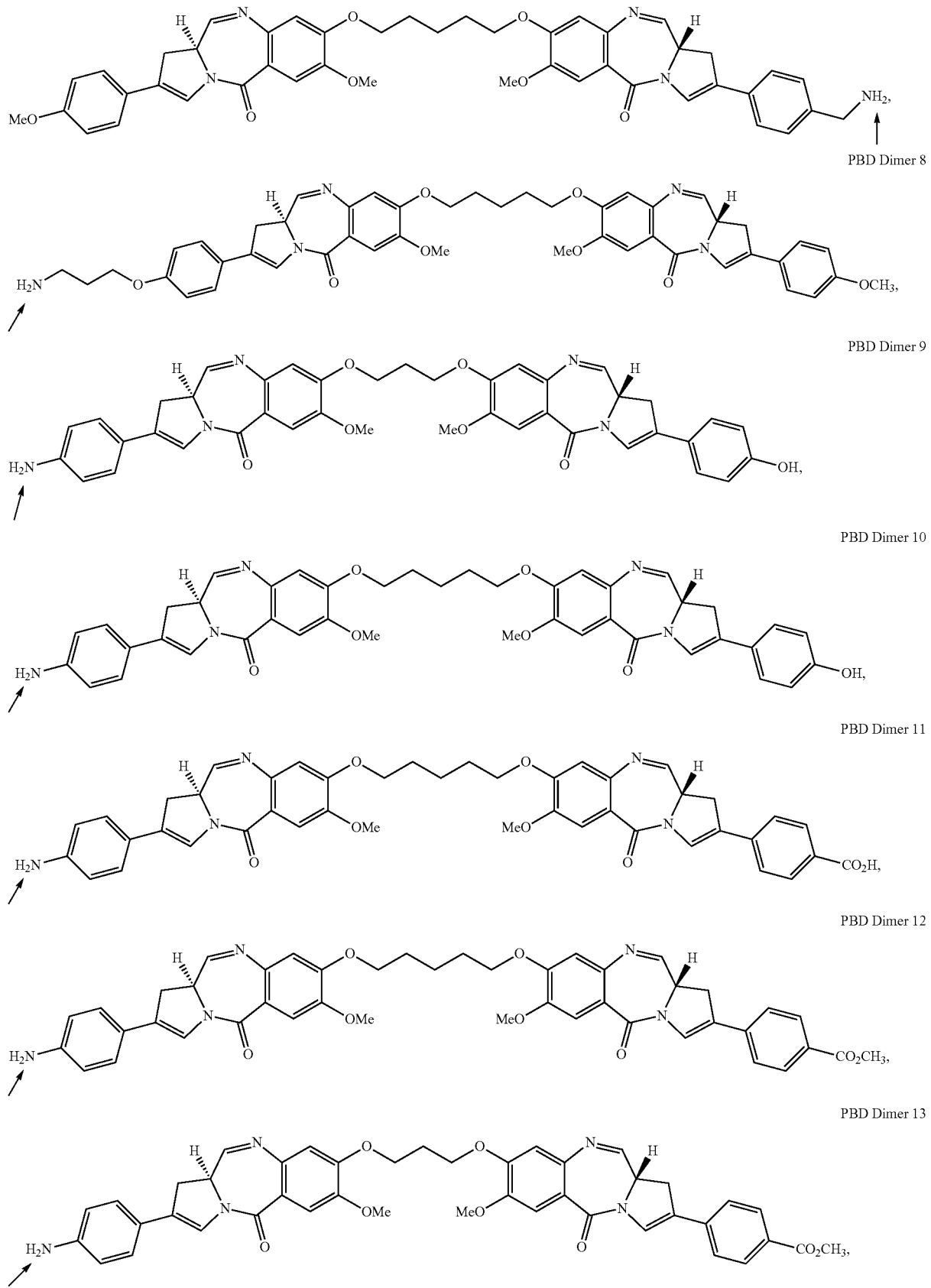

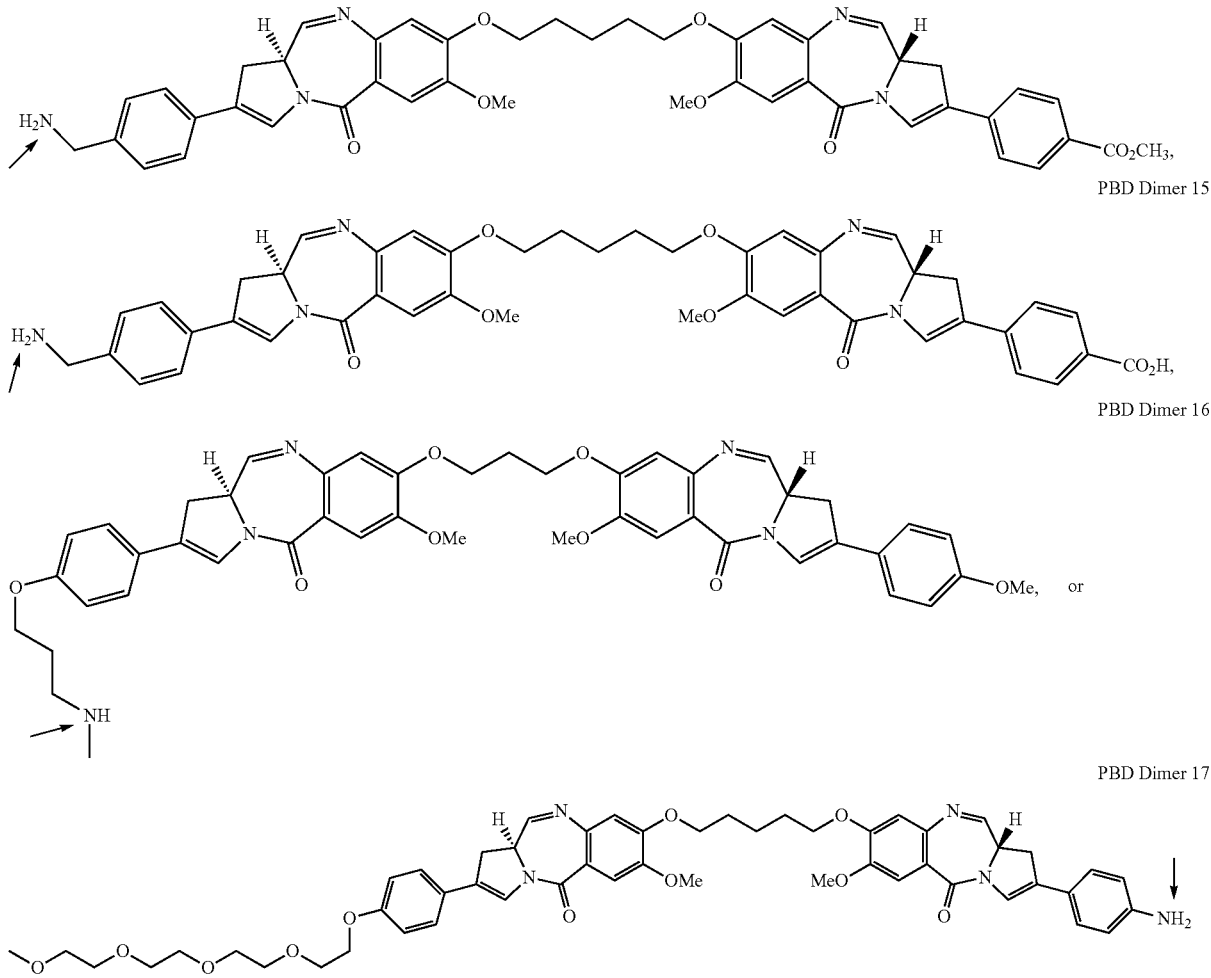

or a salt thereof (e.g., pharmaceutically acceptable salt).

The PBD dimer can be linked to the antibody at any position suitable for conjugation to a linker. For example, in some embodiments, the PBD dimer will have a substituent at the C2 position (e.g., a primary or secondary amine) that provides an anchor for linking the compound to the antibody. The C2 position is marked by an arrow in the exemplary structures shown above. In alternative embodiments, the N10 position of the PBD dimer will provide the anchor for linking the compound to the antibody.

In another aspect, the benzodiazepine dimer is an indolinobenzodiazepine dimer or an oxazolidinobenzodiazepine dimer. Indolinobenzodiazepines (IBDs) and oxazolidinobenzodiazepines (OBDs) are of the general structure:

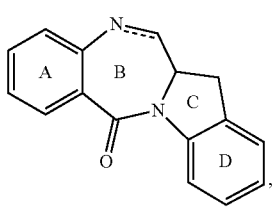

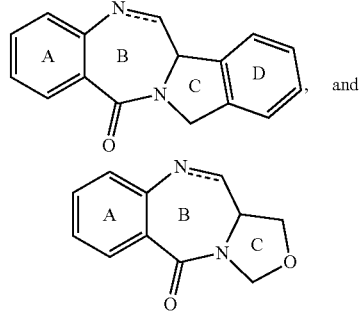

Indolinobenzodiazepines and oxazolidinobenzodiazepines differ in the number, type and position of substituents in their rings. As with the PBDs, two indolinobenzodiazepines or two oxazolidinobenzodiazepines units can be joined together to form dimers, e.g., through ether functionalities between the A rings of two monomeric units. As with the PBDs, an indolinobenzodiazepine dimer or oxazolidinobenzodiazepine dimer can be linked to an antibody at any position suitable for conjugation to a linker.

A benzodiazepine ADC that comprises a PBD dimer as the drug component can also be referred to as a PBD ADC.

Similarly, a benzodiazepine ADC that comprises an indolinobenzodiazepine dimer as the drug component can be referred to as an IBD ADC and an ADC that comprises an oxazolidinobenzodiazepine dimer as the drug component can be referred as an OBD ADC. Typically benzodiazepine ADCs, including PBD ADCs, IBD ADCs and OBD ADCs, comprise a linker between the benzodiazepine drug and the antibody. The linker may comprise a cleavable unit (e.g., an amino acid or a contiguous sequence of amino acids that is a target substrate for an enzyme) or a non-cleavable linker (e.g., linker released by degradation of the antibody). The linker may further comprise a maleimide group for linkage to the antibody, e.g., maleimidocaproyl. The linker may comprise an alternative group for linkage to an antibody, including for example, a N-hydroxyusccinimidyl ester or a labile disulfide, including, for example, a thiopyridyl disulfide. PBD dimers, IBD dimers, OBD dimers, linkers, and conjugates thereof are known in the art. See for example, WO 2010/091150, WO 2012/112708, WO 2012/128868, WO 2011/023883, and WO 2009/016516.

An exemplary linker for linkage of the antibody to the benzodiazepine dimer, including any of those described herein, is as follows wherein the wavy line indicates the site of attachment to the drug and the antibody is linked via the maleimide group.

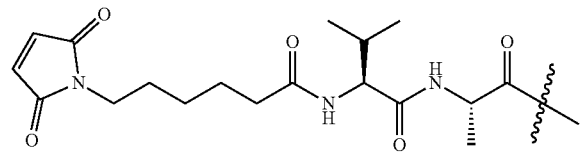 [SMILES: *C(=O)[C@H](C)NC(=O)[C@@H](NC(=O)CCCCCN1C(=O)C=CC1=O)C(C)C]

Exemplary PBD-based antibody-drug conjugates include antibody-drug conjugates as shown below:

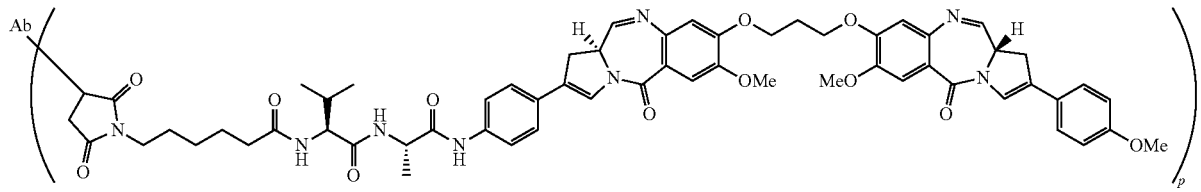

or a salt thereof (e.g., pharmaceutically acceptable salt), wherein Ab is an antibody (e.g., monoclonal antibody) and drug-loading is represented by p, the number of drug-linker molecules per antibody. Depending on the context, p can represent the average number of drug-linker molecules per antibody, also referred to the average drug loading. P ranges from 1 to 20 and is preferably from 1 to 8. In some aspects, when p represents the average drug loading, p ranges from about 2 to about 5. In some aspects, p is about 2, about 3, about 4, or about 5. In some aspects, the antibody is conjugated to the drug linker via a sulfur atom of a cyteine residue. In some aspects the cysteine residue is a cysteine residue of the interchain disulfides of the antibody. In other aspects the cysteine residue is engineered into the antibody. In some aspects, the cysteine residue is engineered into the antibody at position 239 (IgG1) as determined by the EU index (Kabat, *Sequences of Proteins of Immunological Interest* (National Institutes of Health, Bethesda, Md., 1987 and 1991)). In some such aspects, p is about 2. Methods of making such ADCs are known in the art (see, for example, International Publication No. WO2011/130613).

Conjugation Reaction

The present invention is directed, inter alia, to methods for the removal of benzodiazepine drug-related impurities from a mixture comprising benzodiazepine ADCs and benzodiazepine-related impurities. A benzodiazepine drug-related impurity is any drug-related impurity arising from the conjugation reaction of an antibody to a benzodiazepine dimer or benzodiazepine drug-linker. Benzodiazepine drug-related impurities can include, for example, benzodiazepine dimer free drugs, benzodiazepine drug-linkers, quenched benzodiazepine drug-linkers, or benzodiazepine drug-linker degradation products. Benzodiazepine drug-related impurities are not benzodiazepine drugs conjugated to antibodies or drug-linkers conjugated to antibodies.

In some aspects of the present invention, an antibody is contacted with a benzodiazepine drug-linker under conditions sufficient to form a mixture comprising benzodiazepine ADCs and benzodiazepine drug-related impurities (also referred to herein as a conjugation reaction mixture). In other aspects, an antibody-linker (antibody conjugated to a linker) is contacted with a benzodiazepine free drug under conditons sufficient to form a mixture comprising benzodiazepine ADCs and benzodiazepine drug-related impurities (also referred to herein as a conjugation reaction mixture). In other aspects, an antibody-linker is contacted with a benzodiazepine drug-linker under conditions sufficient to form a mixture comprising benzodiazepine ADCs and benzodiazepine drug-related impurities (also referred to herein as a conjugation reaction mixture). General methods of conjugating antibodies to linkers or drug-linkers are known in the art and are not described herein in detail. In some aspects, conjugation will be to the antibody's lysine residues. In other aspects, conjugation will be to a native or engineered cysteine present on the antibody (e.g., cysteine of an inter-chain disulfide or cysteine residue introduced into the heavy or light chain of the antibody). In some aspects, the conjugation will be to an engineered cysteine present on the antibody, the antibody will be reduced prior to contact with the benzodiazepine drug-linker, the antibody will be partially re-oxidized (i.e., re-oxidized as to the inter-chain disulfides but not as to the introduced cysteine) and the benzodiazepine drug-linker will be conjugated to the engineered cysteine on the partially re-oxidized antibody. In some such aspects, the engineered cysteine will be at position 239 (IgG1, EU index numbering as set forth in Kabat).

One of skill in the art will appreciate that the conditions used for conjugating the antibody or antibody-linker to the drug or drug-linker will depend, in part, on the identity of the drug and linker. In general, conjugation reactions are conducted at a temperature of from about 0° C. to about 40° C. In some embodiments, the conjugation reaction is conducted at about 4° C. In some embodiments, the conjugation reaction is conducted at about 25° C. In some embodiments, the conjugation reaction is conducted at about 37° C. The conjugation reactions can be conducted for any suitable length of time. In general, the conjugation reaction mixtures are incubated under suitable conditions for anywhere between a few minutes and several hours. The reactions can be conducted, for example, for about 1 minute, or about 5 minutes, or about 30 minutes, or about 1½ hours, or about 4 hours, or about 12 hours, or about 24 hours. In general, conjugation reaction mixtures are formed with a pH ranging from about 6 to about 9 or from about 7 to about 8. Various buffering agents can be used to maintain a particular pH. Examples of suitable buffering agents include, but are not limited to, 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), sodium citrate, sodium acetate, and sodium borate. Cosolvents (e.g., dimethyl acetamide, propylene glycol, dimethylsulfoxide, dimethylformamide, ethanol, methanol, tetrahydrofuran, acetone, and acetic acid), salts (e.g., NaCl, KCl, $CaCl_2$, and salts of $Mn^{2+}$ and $Mg^{2+}$), chelators (e.g., ethylene glycol-bis(2-aminoethylether)-N,N,N',N'-tetraacetic acid (EGTA), 2-({2-[Bis(carboxymethyl)amino]ethyl}(carboxymethyl)amino)acetic acid (EDTA), and 1,2-bis(o-aminophenoxy)ethane-N,N,N,N-tetraacetic acid (BAPTA)) can also be included as necessary. Buffers, cosolvents, salts, and chelators can be used at any suitable concentration, which can be readily determined by one of skill in the art. In general, buffers, cosolvents, salts, and chelators are included in reaction mixtures at concentrations ranging from about 1 µM to about 1 M or even higher (e.g., 0-50% v/v depending on the co-solvent). Any suitable amount of benzodiazepine drug or drug-linker can be used for conjugation.

In some aspects, following the conjugation reaction (e.g., conjugation of the antibody to the drug-linker), and prior to tangential flow filtration, excess benzodiazepine drug-related impurities will be made unreactive by using a quenching agent. A quenching agent is a reagent, other than an antibody, that is capable of abolishing the reactivity of a reactive moiety by covalently binding to the reactive moiety. One of skill in the art will appreciate that the quenching agent will be chosen based on the nature of the drug or linker. For example, a thiol-containing agent such as such as B-mercapto ethanol or N-acetylcysteine can be used to quench excess drug-linker compound containing a maleimido group or another thiol reactive group. An amine such as glycine can be used to quench excess linker-drug compound containing an N-hydroxysuccinimidyl ester. Typically, the quenching agent is used in excess with respect to the antibody and the drug-linker.

In some aspects, the benzodiazepine drug-related impurity will be a quenched benzodiazepine drug-linker. A quenched conjugation reaction mixture refers to a reaction mixture following the conjugation reaction (e.g., conjugation of the antibody to the drug-linker, the antibody-linker to the drug-linker, or the antibody-linker to the drug), introduction of the quenching agent, and quenching of benzodiazepine drug-related impurities. Typically, the term quenched conjugation reaction mixture refers to the mixture prior to any purification steps.

The benzodiazepine dimers of the present invention are hydrophobic in nature. The present inventors have surprisingly discovered that highly hydrophobic benzodiazepine drug-related impurities can be difficult to remove from ADC mixtures even in instances wherein the benzodiazepine drug-related impurity and ADC are solubilized in the ADC mixture. The present inventions have discovered that benzodiazepine drug-related impurities having a S log P value of less than 7.50 are easier to remove from an ADC mixture using the present methods than benzodiazepine drug-related impurities having a S log P value of greater than 7.50. Accordingly, in preferred embodiments, the benzodiazepine drug-related impurity will have a S log P value of no more than 7.50, more preferably a S log P value of no more than 7.0, even more preferably a S log P value of no more than 6.5 or 6.0, or even 5.8.

The present inventors have further discovered that quenching agents can be used to lower the hydrophobicity of the benzodiazepine drug-related impurities thereby aiding in the purification efforts. By selecting quenching agents that act to reduce the hydrophobicity of the compound to which they bind, the clearance of the benzodiazepine drug-related impurity from the ADC mixture can be improved. Accordingly, particularly preferred quenching agents are those that, when bound to the compound to be quenched, act to reduce the hydrophobicity of the resultant compound. For example, a particularly preferred quenching agent will reduce the hydrophobocity of the benzodiazepine drug-related impurity (e.g., drug or drug-linker) to which it is attached. In some preferred aspects, the quenched benzodiazepine drug-related impurity will have a S log P value of no more than 7.50, more preferably a S log P value of no more than 7.0, even more preferably a S log P value of no more than 6.5 or 6.0, or even 5.8. In some such aspects, the unquenched benzodiazepine drug-related impurity had a higher S log P value than the quenched benzodiazepine drug-related impurity.

S log P is a measure of hydrophobicity. S log P is defined as the log of the octanol/water partition coefficient (including implicit hydrogens) and can be calculated using the program MOE from the Chemical Computing group (S log P values calculated using Wildman, S. A., Crippen, G. M.; Prediction of Physiochemical Parameters by Atomic Contributions; *J. Chem. Inf. Comput. Sci.* 39 No. 5 (1999) 868-873).

Quenching agents that act to reduce the hydrophobicity of the compound to which they bind include charged quenching agents as well as uncharged quenching agents that are nevertheless hydrophilic. Hydrophilic quenching agents include thiol-sugars such as thiol-glucose and PEGylated quenching agents such as PEGylated thiols.

As an example of a PBD drug-linker synthesis, WO 2011/130613 describes a method of synthesizing a PBD drug-linker followed by conjugating the PBD drug-linker to an antibody. Briefly, antibodies in PBS containing 50 mM sodium borate at pH 7.4 are reduced with tris(carboxyethyl) phosphine hydrochloride (TCEP) at 37° C. Antibody interchain disulfides are reformed by oxidation with dehydroascorbic acid, leaving the engineered cysteines in the thiol form available for alkylation with drug linker. The reduced antibody is then alkylated with ~1.5 equivalents of maleimide drug-linker per antibody thiol, in the presence of sufficient co-solvent to solubilize the drug-linker. After about 90 min, the reaction is quenched by the addition of about 3 equivalents of N-acetyl cysteine relative to the drug-linker.

Regardless of the conjugation methods used, benzodiazepine drug-related impurities will be present in the mixture. Generally, but not always, benzodiazepine drug-related impurities will be present in the mixture at levels of about 10 to 100 µM. In some aspects, the benzodiazepine drug-related impurity will be a quenched or unquenched drug-linker, e.g., N-acetyl cysteine quenched drug-linker. In other aspects, the benzodiazepine drug-related impurity will be a quenched or unquenched free benzodiazepine drug (i.e., drug not attached to a linker or antibody). In other aspects, the benzodiazepine drug-related impurity will be a benzodiazepine drug-linker degradation product, such as, for example, an oxidized or hydrolyzed derivative of the drug-linker.

Tangential Flow Filtration (TFF)

Typically following the conjugation reaction and optional quenching, the mixture comprising benzodiazepine ADCs and benzodiazepine drug-related impurities is subjected to tangential flow filtration (TFF). The present inventors have found that, in order to effectively remove drug-related impurities from a mixture, it is preferable to use cyclodextrin and to maintain a minimum level of cyclodextrin throughout the filtration. In order to optimize clearance of the benzodiazepine related impurity, the cyclodextrin is maintained at a level that substantially maintains solubility of the components (e.g., ADC) of the ADC mixture. The cyclodextrin is preferably added to the mixture prior to the start of the filtration process (e.g., after conjugation and optional quenching but prior to initiation of tangential flow filtration) or at the start (or initiation) of the filtration process. In some aspects, cyclodextrin will be added to the ADC mixture after the start of the filtration process but prior to any substantial removal of impurities. The solubilizing agent (e.g., cyclodextrin) is preferably added to the mixture prior to subjecting it to tangential flow filtration. The level of cyclodextrin is preferably maintained throughout the filtration at a minimum level.

The present inventors have found that cyclodextrin is a particularly advantageous solubilizing agent to use as its addition not only improves the removal of benzodiazepine drug-related impurities but its incorporation into the formulated drug-product improves stability of the formulated product. Cyclodextrin can be added to the mixture comprising benzodiazepine ADCs and benzodiazepine drug-related impurities following the conjugation reaction and optional quenching. In some aspects, at least about 1% w/v cyclodextrin (i.e., 10 g per liter) is added to the conjugation reaction mixture. In some aspects, at least about 2% w/v cyclodextrin (i.e., 20 g per liter) is added to the conjugation reaction mixture. In some aspects, at least about 3% w/v cyclodextrin (i.e., 30 g per liter) is added to the conjugation reaction mixture. In some aspects from about 1% w/v cyclodextrin to about 10% w/v cyclodextrin, from about 2% w/v cyclodextrin to about 10% w/v cyclodextrin, or from about 3% w/v cyclodextrin to about 10% w/v cyclodextrin, or from about 3% w/v cyclodextrin to about 6% w/v cyclodextrin or from about 3% w/v cyclodextrin to about 4% w/v cyclodextrin is added to the cyclodextrin mixture.

Tangential flow filtration refers to a filtration process wherein the sample to be purified is re-circulated tangentially past the surface of a semi-permeable membrane. Macromolecules that are too large to pass through the membrane pores are retained on the upstream side (retentate side) of the membrane and molecules that are small enough to pass through the pores pass through to the filtrate side. Generally, determination of which molecules are removed in the filtrate and those molecules retained in the retentate is dependent primarily on molecular weight, solubility, and filter pore size. Other factors such as feed flow rate, transmembrane pressure, membrane type or composition, concentration of components in the fluid mixture, temperature and viscosity of the fluid mixture, can affect the rate and degree of clearance. General methods for using tangential flow filtration devices and performing tangential flow filtration for clearing drug-related impurities from conjugation reaction mixtures are known in the art and can be optimized using the teachings of the present invention combined with the knowledge in the art for use in clearing benzodiazepine drug-related impurities.

In some aspects, the mode of tangential flow filtration will be diafiltration. During diafiltration, buffer is introduced while filtrate is removed. Diafiltration can be, for example, constant volume diafiltration or discontinuous diafiltration. In preferred embodiments, a constant level of cyclodextrin is maintained throughout the diafiltration. In preferred embodiments, cyclodextrin is added to the mixture comprising benzodiazepine ADCs and benzodiazepine drug-related impurities prior to or at the start of the filtration process. In some aspects, a level of at least about 1% w/v cyclodextrin is maintained throughout the filtration. In some such aspects, the ADC mixture is supplemented with cyclodextrin prior to or at the start of the filtration process such that is has a concentration of at least about 1% w/v cyclodextrin and the diafiltration buffer comprises at least about 1% w/v cyclodextrin. In some aspects, a level of at least about 2% w/v cyclodextrin is maintained throughout the filtration. In some such aspects, the ADC mixture is supplemented with cyclodextrin prior to or at the start of the filtration process such that is has a concentration of at least about 2% w/v cyclodextrin and the diafiltration buffer comprises at least about 2% w/v cyclodextrin. In some aspects, a level of at least about 3% w/v cyclodextrin is maintained throughout the filtration. In some such aspects, the ADC mixture is supplemented with cyclodextrin prior to or at the start of the filtration process such that is has a concentration of at least about 3% w/v cyclodextrin and the diafiltration buffer comprises at least about 3% w/v cyclodextrin. In some aspects, a level of at least about 1%, at least about 2%, at least above 3% w/v cyclodextrin is maintained throughout the filtration. In some such aspects, the ADC mixture is supplemented with cyclodextrin prior to or at the start of the filtration process such that is has a concentration of at least about 1%, 2%, or 3% w/v cyclodextrin and the diafiltration buffer comprises at least about 1%, 2%, or 3% w/v cyclodextrin. In other aspects, a level of at from about 1% w/v cyclodextrin to about 10% w/v cyclodextrin, about 2% w/v cyclodextrin to about 10% w/v cyclodextrin, or from about 3% w/v cyclodextrin to about 10% w/v cyclodextrin, or from about 3% w/v cyclodextrin to about 6% w/v cyclodextrin or from about 3% w/v cyclodextrin to about 4% w/v cyclodextrin is maintained throughout the filtration. Preferably, cyclodextrin is added to the ADC mixture prior to or at the start of the filtration process although it is also contemplated that the cyclodextrin is first introduced into the ADC mixture after the start of the filtration process but, preferably, prior to any substantial removal of impurities. Addition of the cyclodextrin can be, for example, via the diafiltration buffer. By the phrase "maintained throughout the filtration", it is mean that the indicated concentration of cyclodextrin is present during the filtration process. In some aspects, such as those wherein the cyclodextrin is added after the initiation of the filtration process (preferably prior to any substantial removal of impurities), the cyclodextrin will not be present at the start of the filtration process but will be maintained at the indicated concentration following introduction of the cyclodextrin.

As noted above, the diafiltration buffer can comprise at least about 1%, at least about 2%, at least about 3% w/v cyclodextrin, or at least about 4% w/v/cyclodextrin. In some aspects, the diafiltration buffer will contain from about 1% w/v cyclodextrin to about 10% w/v cyclodextrin, about 2% w/v cyclodextrin to about 10% w/v cyclodextrin, or from about 3% w/v cyclodextrin to about 10% w/v cyclodextrin, or from about 3% w/v cyclodextrin to about 6% w/v cyclodextrin or from about 3% w/v cyclodextrin to about 4% w/v cyclodextrin. Typically, the diafiltration buffer will additionally comprise a buffering agent. Suitable buffers include, but are not limited to, acetate buffers, phosphate buffers, succinate buffers, histidine buffers, HEPES and MOPS. In one aspect, the buffering agent will be Tris (2-amino-2-(hydroxymethyl)-1,3-propanediol). Exemplary concentrations of buffers for the diafiltration buffer include concentrations of from about 5 mM to about 100 mM, about 50 mM, about 10 mM to about 40 mM, or about 20 mM. With certain embodiments, Tris is included at about 5 mM to about 50 mM, about 10 mM to about 40 mM, or about 20 mM. A suitable pH for a diafiltration buffer is generally in the range of about 6.0 to about 8.0 but can be higher or lower. In some aspects, the pH is in the range of from about 6.5 to about 7.5 or from about 7 to 7.4. In some aspects the pH is about 7.3 or about 7.2.

In some aspects, when using a betacyclodextrin, a concentration of at least about 2%, at least about 3% or at least about 4% of cyclodextrin is maintained throughout the filtration. In some aspects, when using a gamma cyclodextrin, a concentration of at least about 1% is maintained throughout the filtration.

The present invention provides methods for removing benzodiazepine drug-related impurities from an ADC mixture using tangential flow filtration. In some aspects, the tangential flow filtration device comprises a filtration holder having an inlet, a filtrate outlet (also referred to as permeate outlet), a retentate outlet, a semi-permeable ultrafiltration membrane, and a pump. The filtration membrane separates the holder into an upstream compartment and a downstream compartment such that all filtrate must enter the inlet and pass through the membrane before exiting the holder through the filtrate outlet. The filtration membrane to be used can be made out of any material or a combination of materials suitable for use with ADC mixtures. Exemplary membranes include ultrafiltration membranes made out of regenerated cellulose or polyethersulfone (e.g., Millipore ULTRACEL® or BIOMAX® Membranes). The pore size of the membrane refers to the average size of pores in the filter. For use in the present invention, the membrane will typically have a pore size of less than 100 kD, more typically less than about 50 kD, or about 30 kD. Accordingly, in some aspects, the filtration membrane will be a regenerated cellulose or polyethersulfone ultrafiltration membrane having a pore size less than 100 kD, more typically less than about 50 kD, or about 30 kD.

In some aspects, the tangential flow filtration system will further comprise a sample reservoir for holding the conjugation reaction mixture and a buffer reservoir in fluid communication with the buffer reservoir. In some aspects, the purpose of the buffer is for replacing the filtrate volume at the same rate as the filtrate flow such that the volume in the system remains constant. The mixture to be purified will be pumped from the sample reservoir, past the filtration membrane, and returned to the sample reservoir. In some aspects, the flow path will contain a valve that can be used to constrict the return of the mixture to the sample reservoir. Partially closing the valve forces a fraction of the flow through the membrane to waste (filtrate) while the bulk of the flow returns to the sample reservoir (retentate). The filtrate going to waste contains buffer and those solute molecules that are small enough to go through the pores in the membrane. Diafiltration buffer is added to the system to replace the buffer lost as filtrate so the total volume in the system remains constant. Since the diafiltration buffer does not contain the solute being removed, the concentration of solute gradually drops.

As described, in some aspects of the present invention, constant volume diafiltration is the mode of tangential flow filtration that is used to purify the ADC mixture and clear the benzodiazepine drug-related impurities. In constant-volume diafiltration, a diavolume refers to the total solution volume at any one time, in particular the starting total mixture volume. In some aspects, samples will be removed after one or more diavolumes in order to measure the concentration of benzodiazepine drug-related impurities. Diafiltration will typically be run for a number of diavolumes that has been determined by previous experiment to provide clearance to a desired target level. Typically, diafiltration will be terminated once the concentration of benzodiazepine drug-related impurities has reached a target level. In some aspects, a target clearance level is about 1 µM or less, preferably about 0.5 µM or less, 0.2 µM, or even 0.1 µM or less.

In some aspects, the retentate will comprise about 3 mg/ml to about 10 mg/ml benzodiazepine ADC, from about 10 mM to about 30 mM Tris, from about 3% to about 10% w/v cyclodextrin at a pH of from about 6.5 to about 7.5. In some aspects, the retentate will comprise about 3 mg/ml benzodiazepine ADC, about 20 mM Tris, about 3% cyclodextrin or about 4% cyclodextrin, at a pH of about 7.3.

Cyclodextrin

Cyclodextrins are non-reducing cyclic glucose oligosaccharides produced from starch. There are three common cyclodextrins with 6, 7 or 8 glucose units (α-, β-, and γ-cyclodextrin respectively) linked by α-1,4 glycosidic bonds. Cyclodextrins can act as molecular containers by entrapping guest molecules in their internal cavity thereby forming inclusion complexes. The α-cyclodextrins have a smaller cavity whereas the β-, and γ-cyclodextrins have larger cavities.

Suitable cyclodextrins for use in the present invention include alpha, beta, and gamma cyclodextrins, although beta and gamma cyclodextrins are preferred given their larger internal cavities. Chemical modifications have been made to the cyclodextrins, particularly the β-cyclodextrins to improve the solubility of the parent cyclodextrin. Hydroxyethyl β-cyclodextrin, hydroxypropyl β-cyclodextrin (e.g., 2-Hydroxypropyl-β-cyclodextrin), methylated β-cyclodextrin, glucosyl β-cyclodextrin, and sulfobutyl ether β-cyclodextrin are examples of cyclodextrins that have been chemically modified to improve their solubility. In some aspects of the present invention, a β-cyclodextrin including chemically modified β-cyclodextrins will be used. In some aspects, the chemically modified β-cyclodextrin will be hydroxypropyl β-cyclodextrin or sulfobutylether β-cyclodextrin. In some aspects, the cyclodextrin will be a gamma cyclodextrin including chemically modified gamma cyclodextrins. In some aspects, cyclodextrin will be a hydroxypropyl cyclodextrin (e.g., HP4.3-β-cyclodextrin, HP5.5-β-cyclodextrin, HP7.6-β-cyclodextrin, and HP4.5-γ-cyclodextrin). In other aspects, the cylodextrin will be a sulfobuytlether β-cyclodextrins (e.g., SBE6.6-β-cyclodextrin, SBE6.7-β-cyclodextrin, SBE6.8-β-cyclodextrin, SBE4.1-β-cyclodextrin, and SBE4.6Et3.5-β-cyclodextrin). In yet other aspects, the cylodextrin will be a sulfobuytlether γ-cyclodextrins (e.g., SBE4.3-γ-cyclodextrin, SBE4.6-γ-cyclodextrin, SBE5.2-γ-cyclodextrin, and SBE5.6Et6.3-γ-cyclodextrin). As used herein "a chemically modified beta cyclodextrin" is a beta cyclodextrin that has been chemically modified to at least have improved solubility as compared to its parent cyclodextrin (i.e., the unmodified cyclodextrin).

Formulations

The present invention provides mixtures comprising benzodiazepine ADCs and benzodiazepine drug-related impurities (including conjugation reaction mixtures and quenched conjugation reaction mixtures), TFF retentate formulations, and pharmaceutical formulations comprising benzodiazepine ADCs and cyclodextrin. A TFF retentate formulation refers to an ADC mixture that has been purified using TFF but has not been finally formulated.

Cyclodextrins are typically added to the ADC mixtures at levels of at least about 1% w/v, at least about 2% w/v cyclodextrin, at least about 3% w/v cyclodextrin, or at least about 4% w/v cyclodextrin (e.g., at 1% w/v, 2% w/v, 3% w/v, or 4% w/v) In some aspects, the present invention provides a conjugation reaction mixture comprising at least about 1%, at least about 2% w/v cyclodextrin, at least about 3% w/v cyclodextrin, at least about 3% w/v cyclodextrin, a quenched conjugation reaction mixture comprising at least about 1%, at least about 2% w/v cyclodextrin or at least about 3% w/v cyclodextrin, and/or a TFF retentate formulation comprising at least about 1%, at least about 2% w/v cyclodextrin or at least about 3% w/v cyclodextrin. In some aspects, cyclodextrins are present in the ADC mixtures (including conjugation reaction mixtures and quenched conjugation reaction mixtures) and TFF retentate formulations at a level of at from about 2% or about 3% w/v cyclodextrin to about 30% w/v cyclodextrin, from about 2% or about 3% w/v cyclodextrin to about 15% w/v cyclodextrin, from about 2% or about 3% w/v cyclodextrin to about 10% w/v cyclodextrin. In some aspects, wherein the cyclodextrin is a betacyclodextrin there is at least about 2% or about 3% cyclodextrin in the ADC mixture or TFF retentate formulation. In some aspects, wherein the cyclodextrin is a gamma cyclodextrin there is at least about 1% or about 2% cyclodextrin or about 3% cyclodextrin in the ADC mixture or TFF retentate formulation.

Cyclodextrins are typically present in the pharmaceutical formulations at levels of about 3% w/v cyclodextrin or greater. In some aspects, cyclodextrins are present in the pharmaceutical formulations at a level of about 5% w/v or greater, or about 6% w/v or greater. In some aspects, cyclodextrins are present in the pharmaceutical formulations at a level of from about 3% w/v cyclodextrin, about 5% w/v cyclodextrin, or about 6% w/v cyclodextrin to about 30% % w/v cyclodextrin, or from about 3% w/v cyclodextrin, about 5% w/v cyclodextrin, or about 6% w/v cyclodextrin to about 15% % w/v cyclodextrin, or from about 3% w/v cyclodextrin, about 5% w/v cyclodextrin, or about 6% w/v cyclodextrin to about 10% % w/v cyclodextrin, or from about 3% w/v cyclodextrin, about 5% w/v cyclodextrin, or about 6% w/v cyclodextrin to about 8% % w/v cyclodextrin. In some embodiments, the cyclodextrin is present at a concentration of about 3% w/v. In other embodiments, the cyclodextrin is present at a concentration of about 4% w/v. In yet other embodiments, the cyclodextrin is present at a concentration of about 5% w/v, about 6% w/v, about 7% w/v, or about 8% w/v. In some aspects, the pharmaceutical formulations described herein comprise 1 μM or less, 0.5 μM or less, 0.1 μM or less or 0.05 μM or less benzodiazepine drug-related impurities.

In some aspects, the present invention provides benzodiazepine ADC pharmaceutical formulations and TFF retentate formulations comprising 1 μM or less, 0.5 μM or less, 0.1 μM or less or 0.05 μM or less benzodiazepine drug-related impurities. Cyclodextrins can be present in such benzodiazepine ADC formulations, at a level of from about 1%, about 2% or about 3% w/v cyclodextrin to about 30% w/v cyclodextrin, from about 1%, about 2% or about 3% w/v cyclodextrin to about 15% w/v cyclodextrin, from about 1%, about 2% or about 3% w/v cyclodextrin to about 10% w/v cyclodextrin. In some aspects, cyclodextrins are present in the benzodiazepine ADC pharmaceutical formulations and TFF retentate formulations comprising 1 μM or less, 0.5 μM or less, 0.1 μM or less or 0.05 μM or less benzodiazepine drug-related impurities at a level of about 5% or greater, or about 6% or greater. In some aspects, cyclodextrins are present in such formulations at a level of from about 1%, about 2%, about 3% w/v cyclodextrin, about 5% w/v cyclodextrin, or about 6% w/v cyclodextrin to about 30% % w/v cyclodextrin, or from about 3% w/v cyclodextrin, about 5% w/v cyclodextrin, or about 6% w/v cyclodextrin to about 15% % w/v cyclodextrin, or from about 3% w/v cyclodextrin, about 5% w/v cyclodextrin, or about 6% w/v cyclodextrin to about 10% % w/v cyclodextrin, or from about 3% w/v cyclodextrin, about 5% w/v cyclodextrin, or about 6% w/v cyclodextrin to about 8% % w/v cyclodextrin. In some embodiments, the cyclodextrin is present at a concentration of about 1% w/v. In some embodiments, the cyclodextrin is present at a concentration of about 2% w/v. In some embodiments, the cyclodextrin is present at a concentration of about 3% w/v. In other embodiments, the cyclodextrin is present at a concentration of about 4% w/v. In yet other embodiments, the cyclodextrin is present at a concentration of about 5% w/v, about 6% w/v, about 7% w/v, or about 8% w/v.

Pharmaceutical Formulations

The present invention provides pharmaceutical formulations comprising benzodiazepine ADCs and cyclodextrin. The present inventors have discovered that cyclodextrin-containing formulations containing about 2% w/v cyclodextrin or higher exhibit a reduction in the rate and extent of aggregation as compared to formulations containing 0.5% w/v cyclodextrin or less in the formulation and exhibit a reduction of growth of acidic species as compared to formulations containing no cyclodextrin. The present inventors have also discovered that formulations containing about 6% or greater w/v cyclodextrin exhibit a reduction in chemical degradation of the benzodiazepine drug-linker as compared to formulations containing 2% or less w/v cyclodextrin in the formulation. Accordingly, the present invention is based, in part, on the discovery that benzodiazepine ADCs comprising about 6% w/v cyclodextrin exhibit improved stability as compared to formulations containing smaller amounts of cyclodextrin or not containing cyclodextrin at all. Improved stability can be demonstrated, for example, by one or more of the following: (i) reduction of the rate and extent of aggregation, (ii) reduction of growth of acidic species and (iii) reduction of the chemical degradation of the drug. In certain aspects, the present invention provides stabilized liquid or lyophilized benzodiazepine ADC formulations for therapeutic use. In particular, provided are formulations that are stabilized such that a therapeutic benzodiazepine ADC is stable over an extended period of time and can be administered through a variety of administration routes. Such formulations are especially useful, for example, for benzodiazepine ADCs destined for use in the treatment of a disease or disorder (e.g., treatment of a cancer) by exerting a cytotoxic or cytostatic effect on target cells expressing an antigen recognized by the antibody component of the ADC.

In one aspect, the present invention provides a benzodiazepine ADC formulation including a benzodiazepine ADC, a cyclodextrin, and optionally at least one buffering agent, where the buffering agent is present in an amount to maintain a physiologically suitable pH. The cyclodextrin can be any of the cyclodextrins described herein but is preferably a beta or gamma cyclodextrin and more preferably a beta cyclodextrin that has been chemically modified in order to improves its solubility as compared to its parent molecule. In some aspects, the cyclodextrin is a gamma cyclodextrin. In some aspects, the gamma cyclodextrin has been chemically modified in order to improve its solubility as compared to its parent molecule. Particularly preferred cyclodextrins are hydroxypropyl beta cyclodextrin or sulfobutylether beta cyclodextrin. The cyclodextrin can be present in the formulation at any of the concentrations described herein. In some aspects, the cyclodextrin will be a gamma cyclodextrin (unmodified or chemically modified molecule) or a chemically modified beta cyclodextrin (e.g., methylated beta cyclodextrin, glucosyl beta cyclodextrin, hydroxypropyl beta cyclodextrin, or sulfobutyl beta cyclodextrin) present in the formulation at levels of about 3% w/v, about 4% w/v, about 5% w/v, or about about 6% w/v or higher. In some aspects, the cyclodextrin will be a gamma cyclodextrin (unmodified or chemically modified molecule) or a chemically modified beta cyclodextrin (e.g., methylated beta cyclodextrin, glucosyl beta cyclodextrin, hydroxypropyl beta cyclodextrin, or sulfobutyl beta cyclodextrin) present in the formulation at levels of from 3% w/v cyclodextrin, about 5% w/v cyclodextrin, or about 6% w/v cyclodextrin to about 30% % w/v cyclodextrin, or from about 3% w/v cyclodextrin, about 5% w/v cyclodextrin, or about 6% w/v cyclodextrin to about 15% % w/v cyclodextrin, or from about 3% w/v cyclodextrin, about 5% w/v cyclodextrin, or about 6% w/v cyclodextrin to about 10% % w/v cyclodextrin, or from about 3% w/v cyclodextrin, about 5% w/v cyclodextrin, or about 6% w/v cyclodextrin to about 8% % w/v cyclodextrin.

As noted above, an aqueous benzodizepine ADC formulation of the present invention optionally includes a buffering agent to maintain a physiologically suitable pH in aqueous solution. A suitable pH for a stabilized aqueous formulation as described herein includes, e.g., a pH in the range of about 6.0 to about 8.0, or from about 6.5 to about 7.5. In certain embodiments, it may be desirable to formulate the ADC at a pH from about 6.8 to about 7.5; more typically from about 7.0 to about 7.5, from about 7.1 to about 7.5, from about 7.2 to about 7.5, or from about 7.3 to about 7.5. In a particular variation, the pH is about 7.3. In a particular variation, the pH is about 7.2. Suitable buffers include Tris (2-amino-2-(hydroxymethyl)-1,3-propanediol) and citrate, as well as other physiologically acceptable buffers that are effective within the noted pH range and will allow the solution to reach approximately physiological pH during formulation, including upon reconstitution of a lyophilized formulation to form an aqueous solution as described herein. Examples of such buffers include acetate, phosphate, succinate, and histidine. Exemplary concentrations of buffers for formulations in accordance with the present invention are from about 5 mM to about 100 mM, about 50 mM, about 10 mM to about 40 mM, or about 20 mM. With certain embodiments, Tris is included at about 5 mM to about 50 mM, about 10 mM to about 40 mM, or about 20 mM. Other suitable concentrations of buffers for formulations in accordance with the present invention can be readily determined by one of ordinary skill in the art.

In certain variations, formulations—such as those suitable for lyophilization, reconstituted from lyophilized form, or a lyophilized formulation for reconstitution into an aqueous formulation as described herein—may contain one or more stabilizing agents to protect the antibody-drug conjugate. A stabilizing agent is also referred to herein as a lyoprotectant. Typically, a suitable stabilizing agent is a sugar or an amino acid. Exemplary stabilizing agents include sucrose, trehalose, mannitol, sorbitol, dextrose, maltose, dextran, arginine, glycine and histidine. Typically, the amount of stabilizing agent (e.g., lyoprotectant) in a formulation is such that, upon reconstitution, the resulting formulation will be substantially isotonic. In addition, the amount of lyoprotectant must not be too low such that an unacceptable amount of degradation/aggregation of the ADC occurs upon lyophilization. Where the lyoprotectant is a sugar (e.g., sucrose or trehalose), exemplary lyoprotectant concentrations in an aqueous formulation may range from about 1% to about 10% (w/v), more typically about 2% to about 8% (w/v), and even more typically about 4% to about 8% (w/v). In a specific variation, the lyoprotectant is sucrose at a concentration of about 6% (w/v).

In some aspects, there is 0.5 M or less arginine in the formulation. In some aspects, there is 0.2M or 0.1 M or less arginine in the formulation. In some aspects, there is no arginine in the formulation. In some aspects, there are no amino acids in the formulation.

Additional excipients for use in the formulations include, for examples, salts (e.g., sodium chloride), surfactants, (e.g., polysorbate 80, polysorbate 20, poloxamers), antioxidants (e.g, ascorbic acid, methionie, malic acid), and other excipients such as polyethylene glycols, propylene glycols, carboxymethylcellulose, and pyrrolidone.

The ADC concentration in a pharmaceutical formulation of the present invention typically ranges from about 0.1 mg/ml or 0.5 mg/ml to about 50 mg/ml or from about 1 mg/ml to about 30 mg/ml. More typically, the ADC is present at a concentration of from about 1 mg/ml to about 5 mg/ml, to about 10 mg/ml, or to about 15 mg/ml; or at a concentration of from about about 2 mg/ml to about 5 mg/ml or to about 10 mg/ml. In some aspects, the ADC is present at a concentration of from about 0.6 mg/ml to about 3 mg/ml. In particular variations, the ADC is present at a concentration of about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, or about 10 mg/ml.

In some embodiments, the antibody component of the ADC in the ADC mixtures, conjugation reaction mixtures, quenched conjugation reaction mixtures, TFF retentate formulations, and pharmaceutical formulations comprising benzodiazepine ADCs and cyclodextrin described herein is a monoclonal antibody selected from the following: a tetramer consisting of two identical pairs of immunoglobulin chains, each pair having one light chain and one heavy chain; an antibody Fv fragment; an antibody Fab fragment; an antibody Fab'(2) fragment, an antibody Fd fragment, a single-chain antibody (e.g., an scFv or an scFv-Fc fusion); or a single domain antibody fragment (Dab). In a particular variation, the antibody comprises first and second polypeptide chains, where the first polypeptide chain comprises a light chain variable (VL) domain fused at its carboxyl terminus to a light chain constant region, and where the second polypeptide chain comprises a heavy chain variable (VH) domain fused at its carboxyl terminus to a heavy chain constant region. In such variations, the monoclonal antibody is typically a tetramer consisting of two identical pairs of immunoglobulin chains, each pair having one light chain and one heavy chain. The heavy chain constant region may be a naturally-occurring or mutant form of a natural human constant region having reduced binding to an Fcγ receptor relative to the natural human constant region. In some embodiments, the antibody is of an isotype selected from IgG1, IgG2, IgG3, and IgG4. In a specific variation, the heavy chain constant region is of IgG1 isotype.

Various methods for generating antibodies, including monoclonal antibodies, are well-known in the art and are not described herein in detail. Antibodies for use in the present invention can be intact antibodies or antigen binding fragments thereof. Preferred antibodies are human or humanized antibodies, in particular, human or humanized monoclonal antibodies. In some aspects, the antibody will specifically bind to a cancer cell antigen which is expressed on the surface of a cancer cell. In other aspects, the antibody will be bind to activated lymphocytes that are associated with the autoimmune disease state. In some aspects, the antibody will specifically bind CD19, CD20, CD30, CD33, CD70, Glypican-3, Liv-1 or Lewis Y antigen.

In particular embodiments, the antibody is an anti-CD33 antibody that specifically binds to an extracellular domain of human CD33. An exemplary human CD33 sequence is assigned Swiss Prot accession number P20138. In certain embodiments, the anti-CD33 antibody comprises the light and/or heavy chain variable domain complementarity determining regions of the murine anti-CD33 monoclonal antibody designated as 2H12 (VL and VH domain amino acid sequences shown in SEQ ID NOs:1 and 2, respectively). Accordingly, in some variations, the anti-CD33 antibody includes a light chain variable (VL) domain comprising a CDR-L1 amino acid sequence as shown in SEQ ID NO:5, a CDR-L2 amino acid sequence as shown in SEQ ID NO:6, and a CDR-L3 amino acid sequence as shown in SEQ ID NO:7; and/or a heavy chain variable (VH) domain comprising a CDR-H1 amino acid sequence as shown in SEQ ID NO:8, a CDR-H2 amino acid sequence as shown in SEQ ID NO:9, and a CDR-H3 amino acid sequence as shown in SEQ ID NO:10. In some embodiments, the anti-CD33 antibody is a humanized antibody. For example, in certain variations of an anti-CD33 antibody comprising the VL and/or VH domains as above, the VL domain is a humanized VL domain derived from the murine 2H12 VL domain having the amino acid sequence as shown in SEQ ID:1, and/or the VH domain is a humanized VH domain derived from the murine 2H12 VH domain having the amino acid sequence as shown in SEQ ID NO:2. Particularly suitable VL and VH domains have amino acid sequences that are at least 90%, at least 91%, at least 92%, at least 93%, at least 95%, at least 96%, at least 97%, at least 98%, at least 99%, or 100% identical to SEQ ID NO:3 and SEQ ID NO:4, respectively. In certain embodiments, an anti-CD33 antibody includes first and second polypeptide chains, where the first polypeptide chain includes the VL domain fused at its carboxyl terminus to a light chain constant region (e.g., a light chain constant region having the amino acid sequence of SEQ ID NO:21) and the second polypeptide chain includes the VH domain fused at its carboxyl terminus to a heavy chain constant region (e.g., a heavy chain constant region having the amino acid sequence of SEQ ID NO:22 or SEQ ID NO:23). In such variations, the anti-CD33 antibody is typically a tetramer consisting of two identical pairs of immunoglobulin chains, each pair having one light chain and one heavy chain. Exemplary anti-CD33 antibodies suitable for use in accordance with the present invention are also described in US Provisional Application No. 61/649,110, filed on May 18, 2012, the disclosure of which is incorporated by reference herein in its entirety for all purposes.

In other embodiments, the antibody is an anti-CD70 antibody that specifically binds to an extracellular domain of human CD70. An exemplary human CD70 sequence is assigned Swiss Prot accession number P32970.2. In certain embodiments, the anti-CD70 antibody comprises the light and/or heavy chain variable domain complementarity determining regions of the murine anti-CD70 monoclonal antibody designated as 1F6 (VL and VH domain amino acid sequences shown in SEQ ID NOs:11 and 12, respectively). In some such variations, the anti-CD70 antibody includes a light chain variable (VL) domain comprising a CDR-L1 amino acid sequence as shown in SEQ ID NO:15, a CDR-L2 amino acid sequence as shown in SEQ ID NO:16, and a CDR-L3 amino acid sequence as shown in SEQ ID NO:17; and a heavy chain variable (VH) domain comprising a CDR-H1 amino acid sequence as shown in SEQ ID NO:18, a CDR-H2 amino acid sequence as shown in SEQ ID NO:19, and a CDR-H3 amino acid sequence as shown in SEQ ID NO:20. In some embodiments, the anti-CD70 antibody is a humanized antibody. For example, in certain variations of an anti-CD70 antibody comprising the VL and VH domains as above, the VL domain is a humanized VL domain derived from the murine 1F6 VL domain having the amino acid sequence as shown in SEQ ID:11, and/or the VH domain is a humanized VH domain derived from the murine 1F6 VH domain having the amino acid sequence as shown in SEQ ID NO:12. Particularly suitable VL and VH domains have amino acid sequences that are at least 90%, at least 91%, at least 92%, at least 93%, at least 94%, at least 95%, at least 96%, at least 97%, at least 98%, at least 99%, or 100% identical to SEQ ID NO:13 and SEQ ID NO:14, respectively. In certain embodiments, the anti-CD70 antibody includes first and second polypeptide chains, where the first polypeptide chain includes the VL domain fused at its carboxyl terminus to a light chain constant region (e.g., a light chain constant region having the amino acid sequence of SEQ ID NO:21) and the second polypeptide chain includes the VH domain fused at its carboxyl terminus to a heavy chain constant region (e.g., a heavy chain constant region having the amino acid sequence of SEQ ID NO:22). In such variations, the anti-CD70 antibody is typically a tetramer consisting of two identical pairs of immunoglobulin chains, each pair having one light chain and one heavy chain. Exemplary anti-CD70 antibodies suitable for use in accordance with the present invention are also described in U.S. Pat. No. 8,067,546, the disclosure of which is incorporated by reference herein in its entirety for all purposes.

Exemplary anti-CD33 and anti-CD70 variable domain and CDR sequences, as well as exemplary immunoglobulin light and heavy chain constant regions, are shown in Table 1 below.

TABLE 1

| Description | Amino Acid Sequence | SEQ ID NO: |
|---|---|---|
| Murine 2H12 VL | DIKMTQSPSSMYASLGERVIINCKASQDINSYLSWFQQKPGKSPKTLI YRANRLVDGVPSRFSGSGSGQDYSLTISSLEYEDMGIYYCLQYDEFPL TFGAGTKLELK | 1 |
| Murine 2H12 VH | QVQLQQSGPELVRPGTFVKISCKASGYTFTNYDINWVNQRPGQGLEWI GWIYPGDGSTKYNEKFKAKATLTADKSSSTAYLQLNNLTSENSAVYFC ASGYEDAMDYWGQGTSVTVSS | 2 |

TABLE 1-continued

| Description | Amino Acid Sequence | SEQ ID NO: |
|---|---|---|
| Humanized 2H12 VL | DIQMTQSPSSLSASVGDRVTINCKASQDINSYLSWFQQKPGKAPKTLI YRANRLVDGVPSRFSGSGSGQDYTLTISSLQPEDFATYYCLQYDEFPL TFGGGTKVEIK | 3 |
| Humanized 2H12 VH | QVQLVQSGAEVKKPGASVKVSCKASGYTFTNYDINWVRQAPGQGLEWI GWIYPGDGSTKYNEKFKAKATLTADTSTSTAYMELRSLRSDDTAVYYC ASGYEDAMDYWGQGTTVTVSS | 4 |
| 2H12 CDR-L1 | KASQDINSYLS | 5 |
| 2H12 CDR-L2 | RANRLVD | 6 |
| 2H12 CDR-L3 | LQYDEFPLT | 7 |
| 2H12 CDR-H1 | NYDIN | 8 |
| 2H12 CDR-H2 | WIYPGDGSTKYNEKFKA | 9 |
| 2H12 CDR-H3 | GYEDAMDY | 10 |
| Murine 1F6 VL | DIVLTQSPASLAVSLGQRATISCRASKSVSTSGYSFMHWYQQKPGQPP KLLIYLASNLESGVPARFSGSGSGTDFTLNIHPVEEEDAATYYCQHSR EVPWTFGGGTKLEIKR | 11 |
| Murine 1F6 VH | QIQLVQSGPEVKKPGETVKISCKASGYTFTNYGMNWVKQAPGKGLKWM GWINTYTGEPTYADAFKGRFAFSLETSASTAYLQINNLKNEDTATYFC ARDYGDYGMDYWGQGTSVTVSS | 12 |
| Humanized 1F6 VL | DIVMTQSPDSLAVSLGERATINCRASKSVSTSGYSFMHWYQQKPGQPP KLLIYLASNLESGVPDRFSGSGSGTDFTLTISSLQAEDVAVYYCQHSR EVPWTFGQGTKVEIKR | 13 |
| Humanized 1F6 VH | QVQLVQSGAEVKKPGASVKVSCKASGYTFTNYGMNWVRQAPGQGLKWM GWINTYTGEPTYADAFKGRVTMTRDTSISTAYMELSRLRSDDTAVYYC ARDYGDYGMDYWGQGTTVTVSS | 14 |
| 1F6 CDR-L1 | RASKSVSTSGYSFMH | 15 |
| 1F6 CDR-L2 | LASNLES | 16 |
| 1F6 CDR-L3 | QHSREVPWT | 17 |
| 1F6 CDR-H1 | NYGMN | 18 |
| 1F6 CDR-H2 | WINTYTGEPTYADAFKG | 19 |
| 1F6 CDR-H3 | DYGDYGMDY | 20 |
| Human light chain constant region | TVAAPSVFIFPPSDEQLKSGTASVVCLLNNFYPREAKVQWKVDNALQS GNSQESVTEQDSKDSTYSLSSTLTLSKADYEKHKVYACEVTHQGLSSP VTKSFNRGEC | 21 |
| Human heavy chain constant region (no C-term K) | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTC VVVDVSHEDPEVKFNWYVDGVEVHNAKTKPREEQYNSTYRVVSVLTVL HQDWLNGKEYKCKVSNKALPAPIEKTISKAKGQPREPQVYTLPPSRDE LTKNQVSLTCLVKGFYPSDIAVEWESNGQPENNYKTTPPVLDSDGSFF LYSKLTVDKSRWQQGNVFSCSVMHEALHNHYTQKSLSLSPG | 22 |

TABLE 1-continued

| Description | Amino Acid Sequence | SEQ ID NO: |
|---|---|---|
| Human heavy chain constant region, S239C (no C-term K) | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KVEPKSCDKTHTCPPCPAPELLGGPCVFLFPPKPKDTLMISRTPEVTC VVVDVSHEDPEVKFNWYVDGVEVHNAKTKPREEQYNSTYRVVSVLTVL HQDWLNGKEYKCKVSNKALPAPIEKTISKAKGQPREPQVYTLPPSRDE LTKNQVSLTCLVKGFYPSDIAVEWESNGQPENNYKTTPPVLDSDGSFF LYSKLTVDKSRWQQGNVFSCSVMHEALHNHYTQKSLSLSPG | 23 |

As previously noted, exemplary pharmaceutical formulations of the present invention exhibit (i) a reduction in the rate and extent of aggregation as compared to formulations containing 0.5% w/v cyclodextrin or less in the formulation, (ii) a reduction of growth of acidic species as compared to formulations containing no cyclodextrin and/or (iii) a reduction in chemical degradation of the drug-linker (e.g., the benzodiazepine drug) as compared to formulations containing 2% or less w/v cyclodextrin in the formulation. Accordingly, the present invention provides methods for preparing a formulation that has at least one of (i) improved resistance to chemical degradation of the benzodizepine drug as compared to formulations containing 2% or less w/v cyclodextrin in the formulation, (ii) improved resistance to aggregation as compared to formulations containing 0.5% w/v cyclodextrin or less in the formulation, and (iii) improved resistance to growth of acidic species as compared to formulations containing no cyclodextrin. Accordingly, in some aspects, pharmaceutical formulations of the present invention comprising about 5% or about 6% w/v or more cyclodextrin exhibit at least one of (i) improved resistance to chemical degradation of the benzodiazepine drug as compared to formulations containing 2% or less cyclodextrin, (ii) improved resistance to aggregation as compared to formulations containing 0.5% or less cyclodextrin and (iii) improved resistance to growth of acidic species compared to formulations containing 0.5% or less cyclodextrin. Accordingly, in some aspects, pharmaceutical formulations of the present invention comprising about 5% or about 6% w/v or more cyclodextrin exhibit (i) improved resistance to chemical degradation of the benzodiazepine drug as compared to formulations containing 2% or less cyclodextrin, and (ii) improved resistance to aggregation as compared to formulations containing 0.5% or less cyclodextrin. In other aspects, pharmaceutical formulations of the present invention comprising about 5% or about 6% w/v or more cyclodextrin exhibit (i) improved resistance to chemical degradation of the benzodiazepine drug as compared to formulations containing 2% or less cyclodextrin, (ii) improved resistance to aggregation as compared to formulations containing 0.5% or less cyclodextrin and (iii) improved resistance to growth of acidic species compared to formulations containing 0.5% or less cyclodextrin.

In any of the mixtures or formulations described herein (including pharmaceutical formulations), the benzodiazepine ADC can comprise a humanized 2H12 or humanized 1F6 antibody conjugated to PBD Dimer 1, PBD Dimer 2, PBD Dimer 3, PBD Dimer 4, PBD Dimer 5, PBD Dimer 6, PBD Dimer 7, PBD Dimer 8, PBD Dimer 9, PBD Dimer 10, PBD Dimer 11, PBD Dimer 12, PBD Dimer 13, PBD Dimer 14, PBD Dimer 15, PBD Dimer 16, or PBD Dimer 17 as described herein. In some aspects, conjugation of the PBD Dimer to the antibody will be via a cysteine residue engineered into the antibody. In some aspects, the cysteine residue is engineered into the antibody at position 239 (human IgG1) as determined by the EU index (Kabat, Sequences of Proteins of Immunological Interest (National Institutes of Health, Bethesda, Md., 1987 and 1991)). In some aspects, there will be an average 2 drug-linkers per antibody in the formulation.

In some embodiments, a pharmaceutical formulation of the present invention provides a concentrated preparation of an ADC (for example, an anti-CD33 or anti-CD70 ADC), often useful as bulk drug product. Furthermore, in certain embodiments, a pharmaceutical formulation of the present invention is stable to freezing, lyophilization and/or reconstitution.

In some aspects, the pharmaceutical formulations described herein are stored at temperatures from about −80° C. to about 8° C. Generally, the pharmaceutical formulation is stable and retains biological activity at these ranges. In certain aspects, the formulations decribed herein have improved stabilty as compared to formulations not containing cyclodextrin when exposed to stress conditions (e.g., storage at 25° C. or 40° C. for extended period of times such as 7 days and 14 days)

The pharmaceutical formulations of the present invention are suitable for delivery by a variety of administration routes. In certain embodiments, the pharmaceutical formulation is administered parenterally, such as intravenously, intramuscularly, or subcutaneously. For administration of an ADC for the treatment of cancer, the pharmaceutical formulation may be delivered into the systemic circulation by intravenous or subcutaneous administration. In a particular embodiment, the pharmaceutical formulation is formulated for intravenous delivery. Intravenous administration can be, for example, by infusion over a period such as 30-90 minutes or by a single bolus injection. In some aspects, administration will be via slow IV push (i.e., over 30-60 seconds) in a peripherally inserted central catheter.

Effective doses of the pharmaceutical formulations of the present invention vary depending upon many different factors, including means of administration, target site, physiological state of the patient, whether the patient is human or an animal, other medications administered, and whether treatment is prophylactic or therapeutic. Usually, the patient is a human but non-human mammals can also be treated. Treatment dosages need to be titrated to optimize safety and efficacy.

Exemplary dosages for the ADC formulations of the present invention include from about 1.0 µg/kg to about 5 mg/kg, from about 10 µg/kg to about 3 mg/kg, from about 10 µg/kg to about 2 mg/kg, from about 1.0 µg/kg to 1.0 mg/kg, or from about 1.0 µg/kg to 500.0 µg/kg of the subjects body weight.

The frequency of administration depends on the half-life of the antibody-drug conjugate in the circulation, the condition of the patient, and the route of administration, among other factors. The frequency can be daily, weekly, monthly, quarterly, or at irregular intervals in response to changes in the patient's condition or progression of the condition (e.g., cancer) being treated. An exemplary frequency for intravenous administration is between twice a week and quarterly over a continuous course of treatment, although more or less frequent dosing is also possible. Other exemplary frequencies for intravenous administration are between once weekly or once monthly over a continuous course of treatment, although more or less frequent dosing is also possible. For subcutaneous administration, an exemplary dosing frequency is daily to monthly, although more or less frequent dosing is also possible.

It is especially advantageous to provide the formulations of the invention in unit dosage form for ease of administration and uniformity of dosage. Formulations of the invention may be presented in either liquid or lyophilized form in, e.g., capsules, glass vials, ampules, multi-dose containers, or the like. The unit dosage form may comprise any formulation described herein. In some aspects, the ADC will be as a lyophilized cake or powder stored in a single-use amber glass for reconstitution for IV administration. Reconstitution is with a suitable diluent (e.g., Water For Injection) to the desired concentration. Typically the reconstituted is reconstituted with sufficient diluent such that the reconstituted solution will have the same concentration of components as the formulation prior to lyophilization. The reconstituted product may be further diluted depending on the dose level to be administered to the patient. Further dilution can be with, for example, Sodium Chloride for Injection. In some aspects of the invention, immediately following reconstitution or optional further dilution, the ADC is administered by IV (e.g., slow IV push) into an appropriate injection port of a central venous access device. The infusion line will typically be flushed with saline.

In some aspects, the present invention provides a therapeutic product that includes a pharmaceutical dosage unit form comprising a stabilized ADC formulation of the present invention (e.g., a sealed container containing an ADC formulation, in either liquid or lyophilized form, as described herein). The therapeutic product can further include labeling for use. In some embodiments, the therapeutic product is provided as a kit further including, for example, instructions to use the appropriate volume necessary to achieve a therapeutic dose in a patient. The unit dosage form, container, or kit may be designed to provide enough formulation for multiple uses or may be for single use. In some embodiments, the kit further includes a diluent.

If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims. All patent filings, website, other publications, accession numbers and the like cited above or below are incorporated by reference in their entirety for all purposes to the same extent as if each individual item were specifically and individually indicated to be so incorporated by reference.

EXAMPLES

PBD dimers 1-4 and the synthesis thereof are described in WO2011/130613. PBD dimers 5-10 and 16 can be synthesized using the methods described in WO2011/130613 A1. Briefly, PBDs dimers 9 and 16 are accessible through the C3-tethered bis-triflate intermediate 8a in WO2011/130613 A1. The desired C2 aryl groups as boronic acids or pinacol boronates are introduced in sequential Suzuki couplings, followed by SEM dilactam reduction to reveal the imine functional groups. PBD dimers 5-8 and 10 are prepared in the same manner from C5-tethered bis-triflate intermediate 8b in WO2011/130613 A1. PBD dimers 11-15 containing esters or carboxylic acids in the C2 aryl groups can be accessed using the methods described in WO2011/130613 A1 with minor modifications. PBD dimer 13 can be prepared from the C3-tethered bis-triflate intermediate 8a in WO2011/130613 A1. The bis triflate is desymmetrized via Suzuki coupling with an appropriately functionalized boronic acid or pinacol boronate to install the C2 aryl group bearing the amino functional group. The resulting monotriflate is then reduced with lithium triethylborohydride to the SEM carbinol, which is then carried forward to the second Suzuki coupling to install the C2 aryl group containing the methyl ester. Finally, the SEM carbinols are converted to imines via stirring on silica gel for 3 days, as described in WO2011/130613 A1. PBD dimers 12 and 14 can be prepared in the same way starting with C5-tethered bis triflate 8b in WO2011/130613 A1. Conversion of the PBD esters to the free carboxylic acid (11 and 15) could be achieved via saponification. Preparation of cysteine mutants of IgG1 mAb is generally described in US20100158909.

The PBD drug-linkers used in the following examples are as follows. Conjugation of the drug-linkers to the antibodies is as described in WO2011/130613 A1.

Compound 1

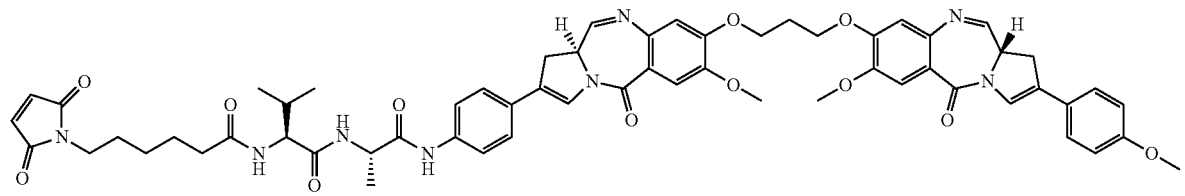

-continued

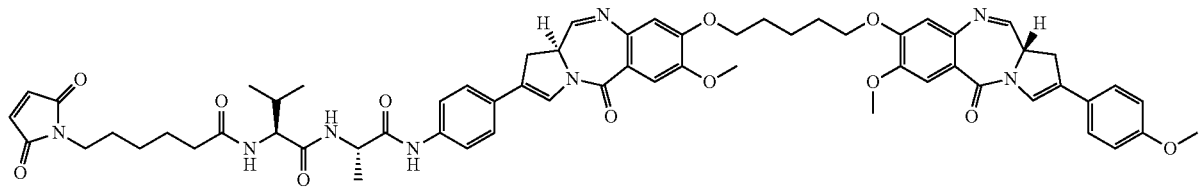
Compound 2

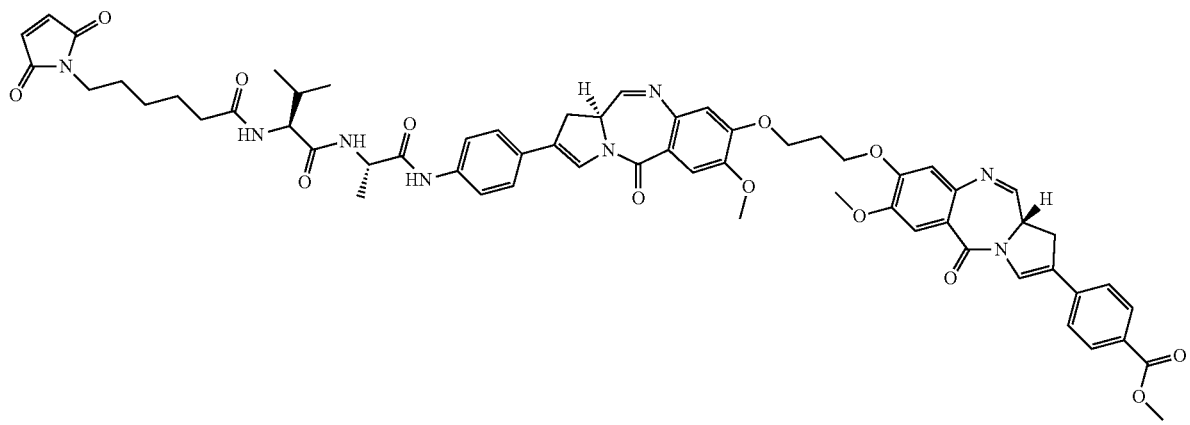
Compound 3

The quenched drug-linker referred to in the following examples has the following structure:

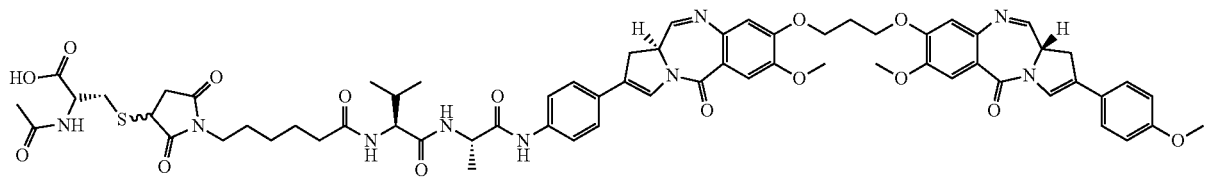
Compound 4

The PBD drug linkers were conjugated to the h2H12ec antibody or h1F6ec via position 239 of the heavy chain (The notation "ec" following the antibody name refers to an antibody having an engineered cysteine at position 239.) Briefly, the h2H12 and h1F6 having an introduced cysteine at position 239 (EU index numbering) were reduced, partially re-oxidized (i.e., re-oxidized as to inter-chain disulfides), and conjugated to the PBD drug-linker using methods described in WO 2011/130613 to form an ADC. The PBD drug-linker was conjugated to the partially re-oxidized antibody via the introduced cysteine residues (average of 2 drug-linkers per antibody). h2H12-1 refers to the humanized 2H12ec antibody conjugated to compound 1 whereas h1F6-1 refers to the humanized 1F6ec antibody conjugated to compound 1. h2H12-2 refers to the humanized 2H12ec antibody conjugated to compound 2 whereas h1F6-2 refers to the humanized 1F6ec antibody conjugated to compound 2. h2H12-3 refers to the humanized 2H12ec antibody conjugated to compound 3 whereas h1F6-3 refers to the humanized 1F6ec antibody conjugated to compound 3. Examples 4-7 were performed using either the h2H12ec or h1F6ec antibody conjugated to compound 1 via the introduced cysteine at position 239.

Figure 2:
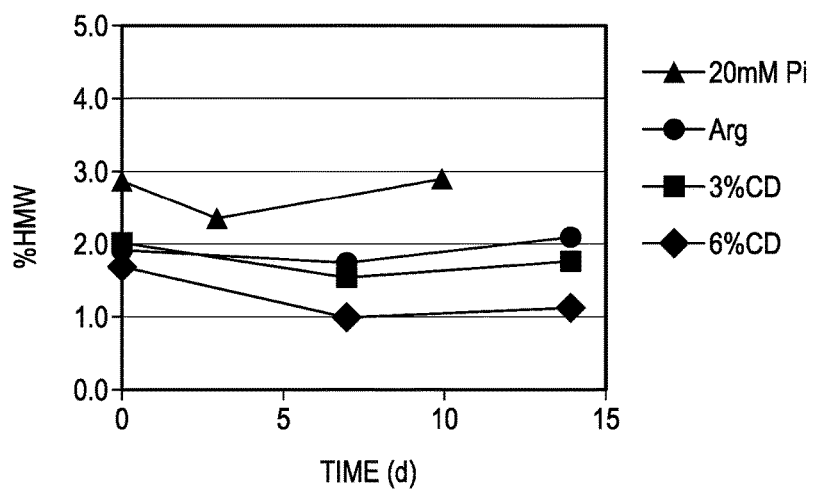
FIG. 2 provides a graph showing the percent high molecular weight (% HMW) species present in various h1F6-1 formulations stored at 25° C. % HMW is determined at time points 0, 7 days, and 14 days.
Figure 3:
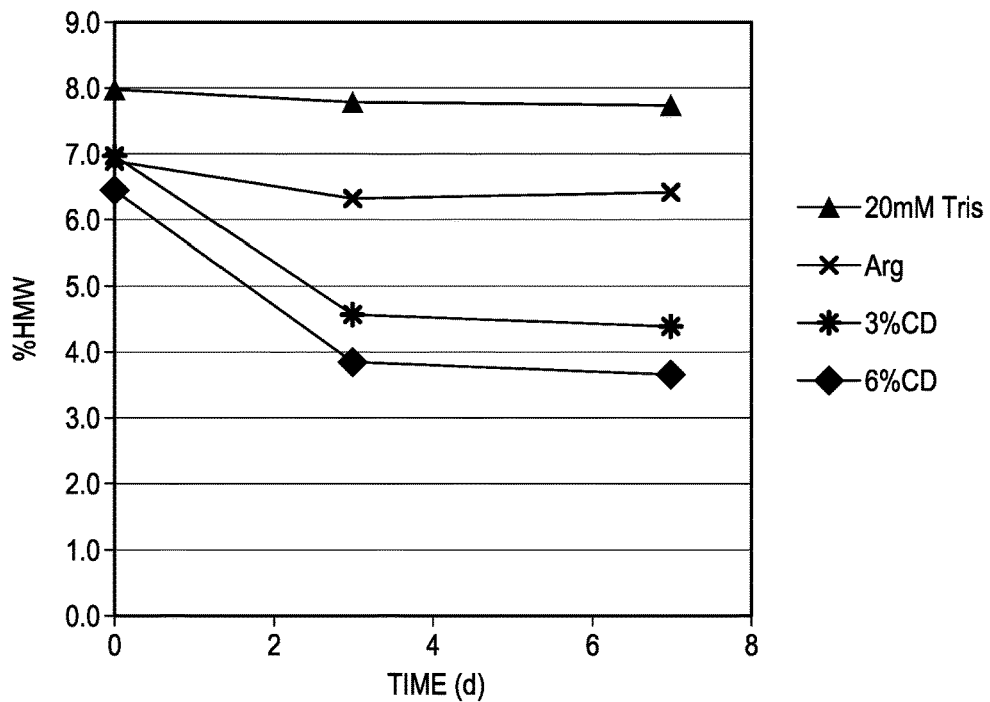
FIG. 3 provides a graph showing the percent high molecular weight (% HMW) species present in various h2H12-3 formulations stored at 40° C. % HMW is determined at time points 0, 3 days, and 7 days.
Figure 4:
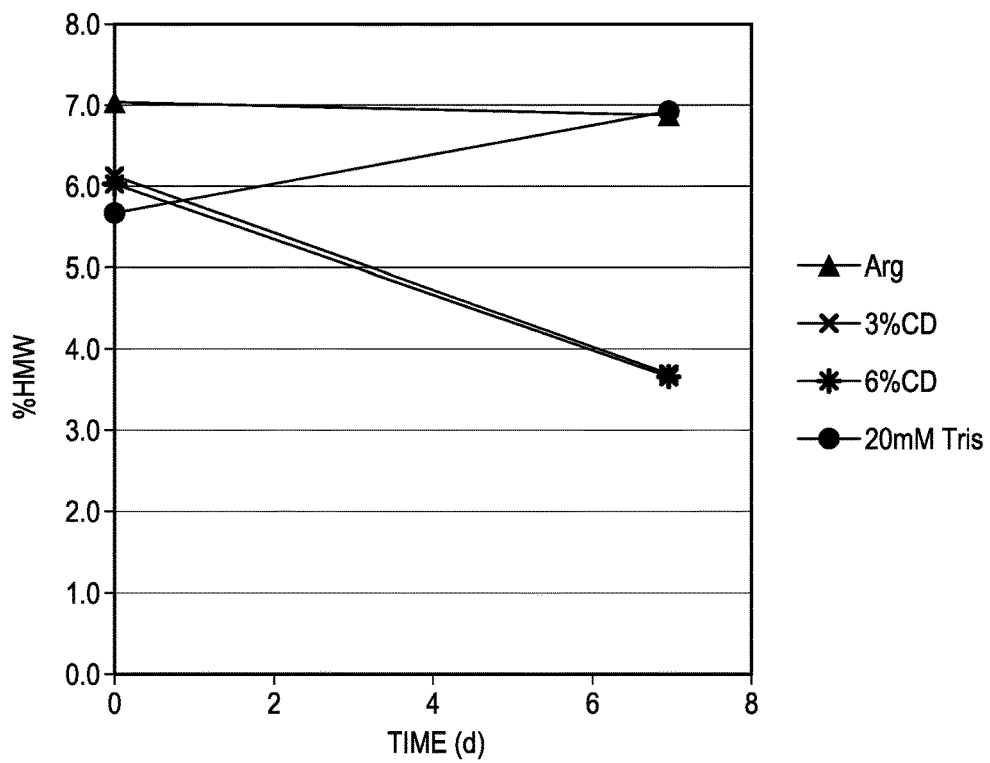
FIG. 4 provides a graph showing the percent high molecular weight (% HMW) species present in various h1F6-3 formulations stored at 40° C. % HMW is determined at time points 0, 3 days, and 7 days.
Figure 5:
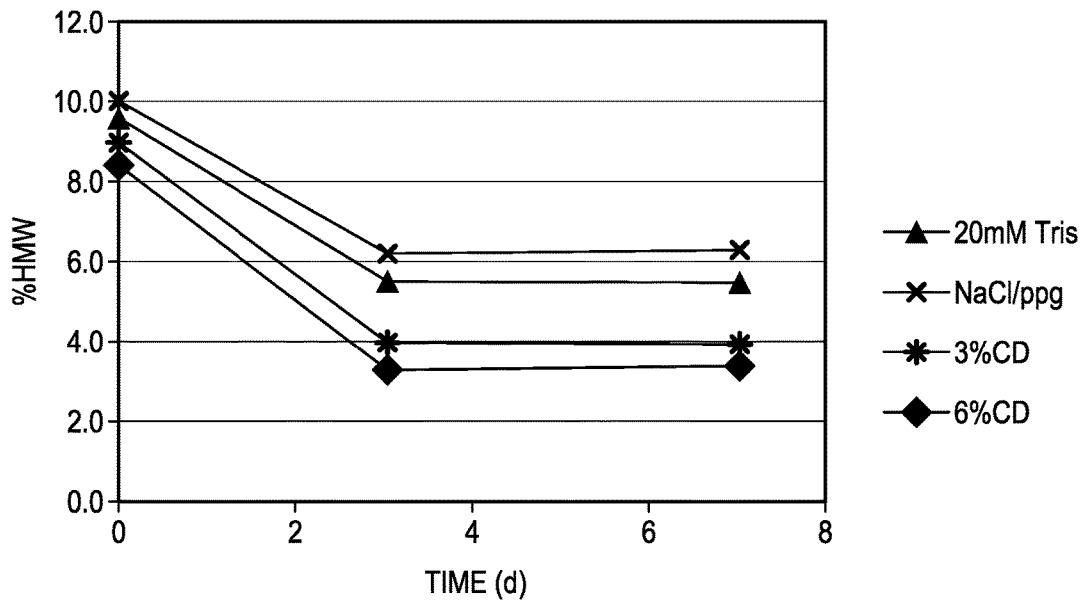
FIG. 5 provides a graph showing the percent high molecular weight (% HMW) species present in various h2H12-2 formulations stored at 40° C. % HMW is determined at time points 0, 3 days, and 7 days.
Figure 6:
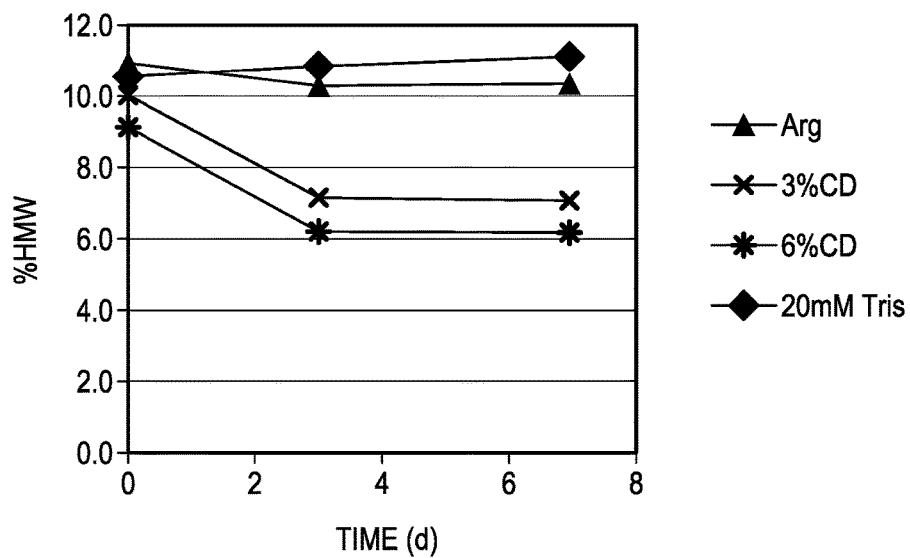
FIG. 6 provides a graph showing the percent high molecular weight (% HMW) species present in various h1F6-2 formulations stored at 40° C. % HMW is determined at time points 0, 3 days, and 7 days.
Figure 13:
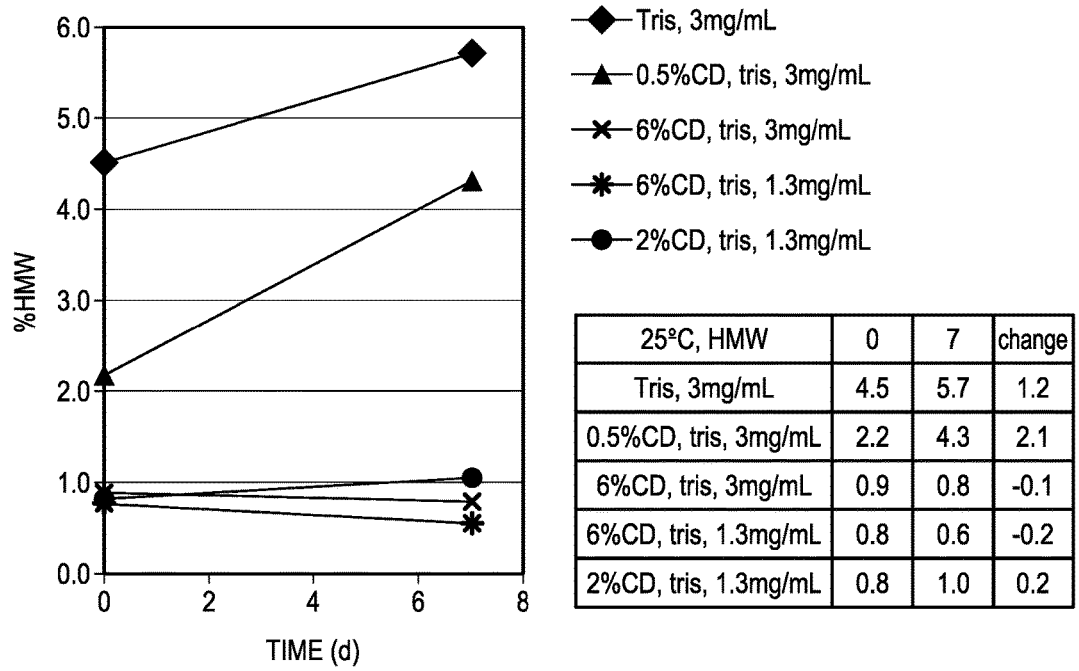
FIG. 13 provides a graph showing the percent high molecular weight (% HMW) species present in various h1F6-1 formulations stored at 25° C. % HMW is determined at time points 0 and 7 days.

Example 1: Cyclodextrin Based Formulations Reduced the Rate and Extent of Aggregation for all Six PBD ADCs Formulations were prepared by buffer exchange of starting materials into the tested formulation buffers using dialysis, buffer exchange column or centrifugal filtration. The formulations are as indicated in the figure legends. The concentration of arginine when indicated as present is at 0.5 M. Final ADC concentration was in the range of 1.3 mg/mL to 3.1 mg/mL determined by UV spectrometry. The formulated ADCs were filled into pre-sterilized tubes and stored at the following ICH conditions: 2-8° C., 25° C./65% RH and/or 40° C./75% RH. % HMW was monitored using size exclusion chromatography. FIG. 1 formulations contain h2H12-1 and storage is at 25° C.; FIG. 2 formulations contain h1F6-1 and storage is at 25° C.; FIG. 3 formulations contain h2H12-3 and storage is at 40° C.; FIG. 4 formulations contain h1F6-3 and storage is at 40° C.; FIG. 5 formulations contain h2H12-2 and storage is at 40° C.; FIG. 6 formulations contain h1F6-2 and storage is at 40° C.; FIG. 13 formulations contain h1F6-1 and storage is at 25° C.

Figure 7:
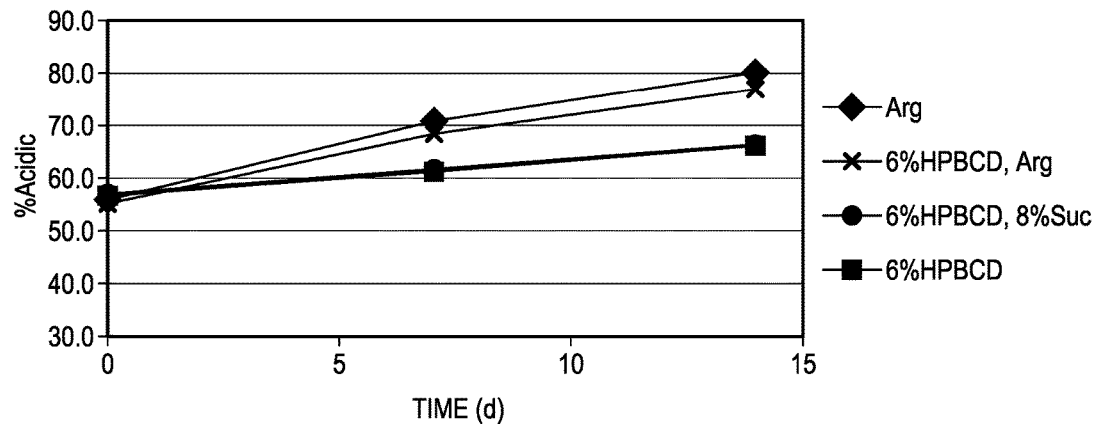
FIG. 7 provides a graph showing the percent acidic species present in various h2H12-1 formulations stored at 25° C. Percent acidic species is determined at time points 0, 7 days, and 14 days.
Figure 8:
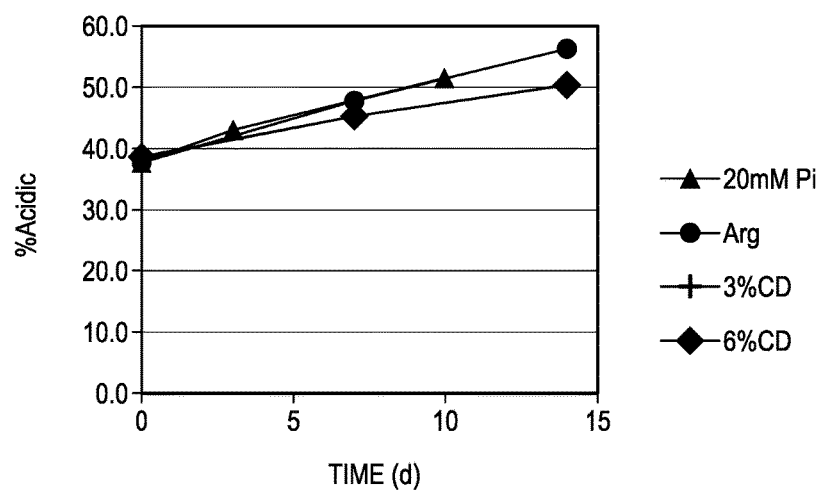
FIG. 8 provides a graph showing the percent acidic species present in various h21F6-1 formulations stored at 25° C. Percent acidic species is determined at time points 0, 7 days, and 14 days.
Figure 9:
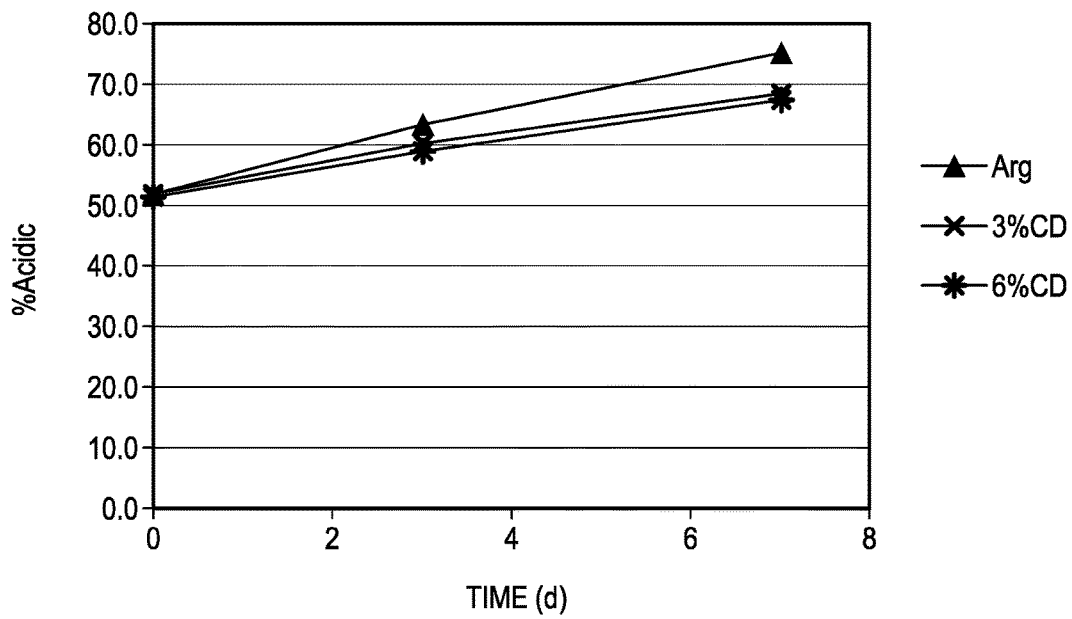
FIG. 9 provides a graph showing the percent acidic species present in various h2H12-3 formulations stored at 40° C. Percent acidic species is determined at time points 0, 3 days, and 7 days.
Figure 10:
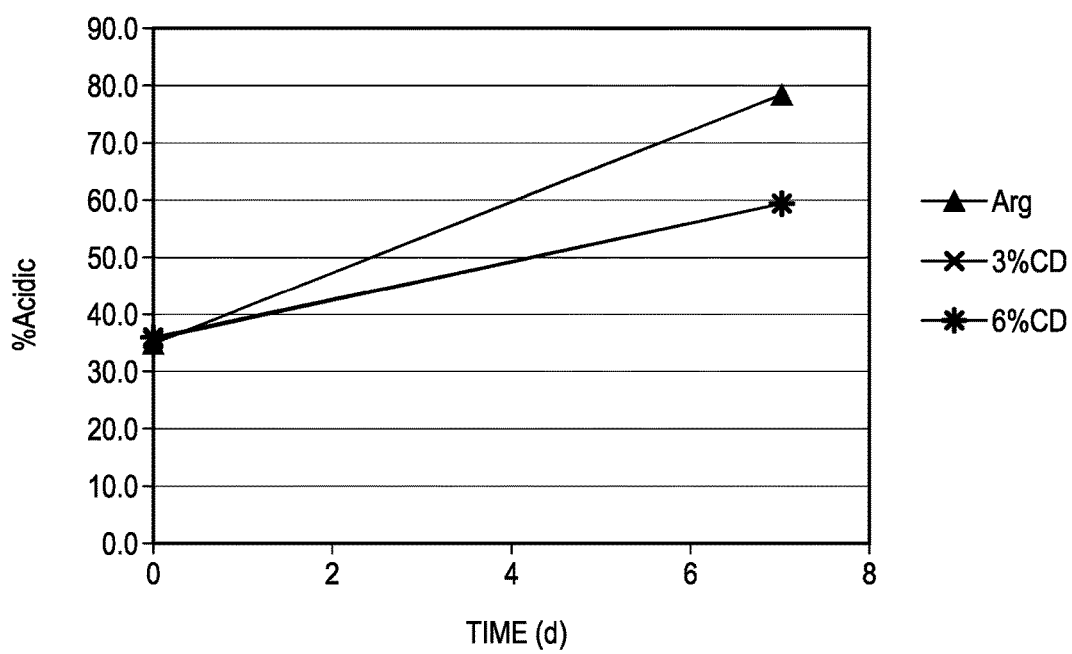
FIG. 10 provides a graph showing the percent acidic species present in various h1F6-3 formulations stored at 40° C. Percent acidic species is determined at time points 0, 3 days, and 7 days.
Figure 11:
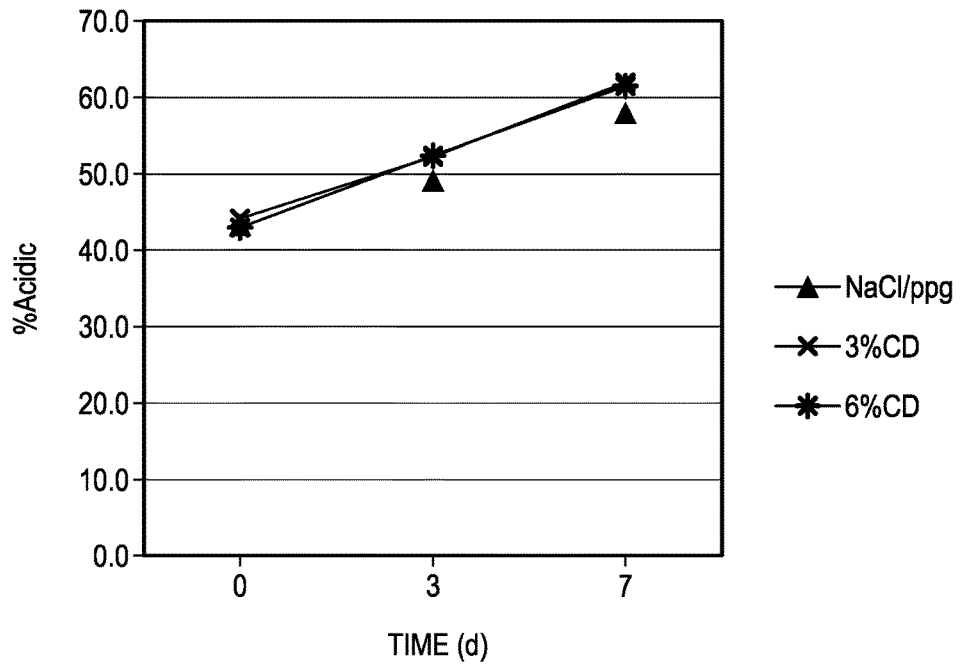
FIG. 11 provides a graph showing the percent acidic species present in various h2H12-2 formulations stored at 40° C. Percent acidic species is determined at time points 0, 3 days, and 7 days.
Figure 12:
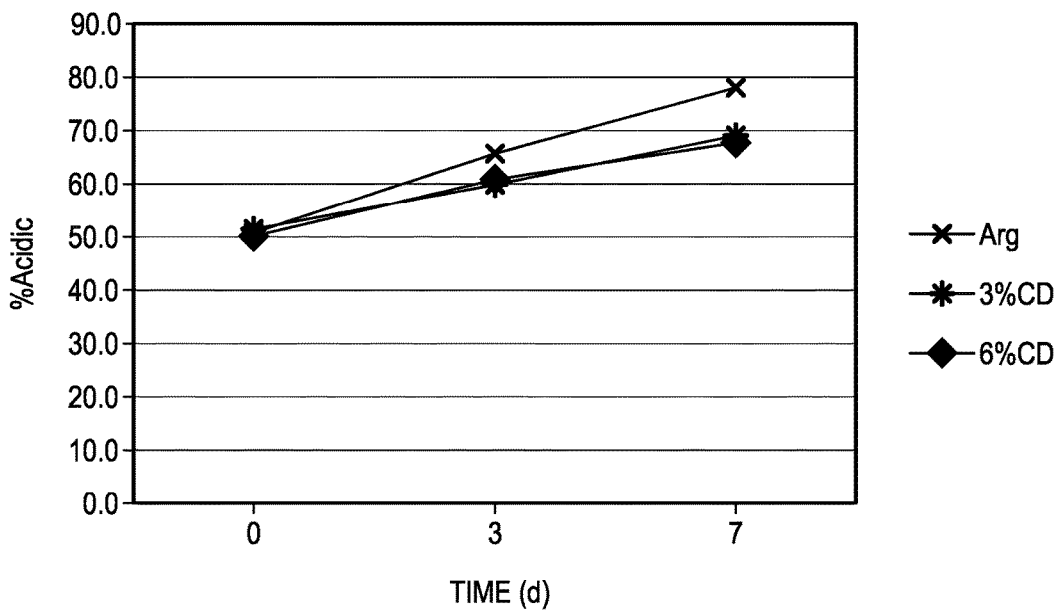
FIG. 12 provides a graph showing the percent acidic species present in various h21F6-2 formulations stored at 40° C. Percent acidic species is determined at time points 0, 3 days, and 7 days.

Example 2: HPBCD-Based Formulations Reduced the Growth of Acidic Species for Five of of Six PBD ADCs Formulations were prepared by buffer exchange of starting materials into the tested formulation buffers using dialysis, buffer exchange column or centrifugal filtration. The formulations are as indicated in the figure legends. The concentration of arginine when indicated as present is at 0.5 M. Final ADC concentration was in the range of 1.3 mg/mL to 3.1 mg/mL determined by UV spectrometry. The formulation were filled into pre-sterilized tubes and stored at the following ICH conditions: 2-8° C., 25° C./65% RH and/or 40° C./75% RH. Samples were analyzed for charge distribution (% acidic, % main, % basic) by image capillary isoelectric focusing. FIG. 7 formulations contain h2H12-1 and storage is at 25° C.; FIG. 8 formulations contain h1F6-1 and storage is at 25° C.; FIG. 9 formulations contain h2H12-3 and storage is at 40° C.; FIG. 10 formulations contain h1F6-3 and storage is at 40° C.; FIG. 11 formulations contain h2H12-2 and storage is at 40° C.; FIG. 12 formulations contain h1F6-2 and storage is at 40° C.

Example 3: HPBCD-Based Formulations Reduced the Chemical Degradation of the Drug-Linker Formulations were prepared by buffer exchange of starting materials into the tested formulation buffers using dialysis, buffer exchange column or centrifugal filtration. In general, formulations included initial formulation as control (mostly arginine), buffer, 3% cyclodextrin and 6% cyclodextrin. Final ADC concentration was in the range of 1.3 mg/mL to 3.1 mg/mL determined by UV spectrometry. The formulation were filled into pre-sterilized tubes and stored at the following ICH conditions: 2-8° C., 25° C./65% RH and/or 40° C./75% RH. Drug-linker stability was measured by % degradants using reduced PLRP/MS or by % intact drug linker using pepsin digest map. The results are as follows with the formulations listed in the left-hand column. Table 2 demonstrates that formulation containing 6% cyclodextrin demonstrated less drug linker degradation than that with 2% cyclodextrin after 1 week at 40° C. Table 3 demonstrates that formulations of h2H12-1 containing 6% cyclodextrin demonstrated less drug linker degradation after 1 week at 25° C. and Table 4 demonstrates that the formulations of h1F6-1 containing 6% hbcyclodextrin maintained higher level of intact drug linker after 1 week of incubation at 40° C.

TABLE 2

| h1F6-1 sample (after 1 week storage at 40° C.) | % of intact drug-linker by pepsin digest |
| --- | --- |
| Starting material (T0 control) | 82 |
| 20 mM Tris, 2% CD | 63 |
| 20 mM Tris, 6% CD | 70 |

TABLE 3

| h2H12-1 sample (after 1 week storage at 25° C.) | % of drug linker degradant (−168 dalton species) |
| --- | --- |
| 0.5M Arg [t = 0, Control] | 0.2 |
| 0.5M Arg [25° C., t = 1 w] | 4.7 |
| 0.5M Arg, 6% hpβCD [25° C., t = 1 w] | 3.0 |
| 6% hpβCD, 20 mM KPhos [t = 0, Control] | 0.6 |
| 6% hpβCD, 20 mM KPhos [25° C. t = 1 w] | 1.4 |

TABLE 4

| h1F6ec-1 sample (after 1 week storage at 40° C.) | % of intact drug-linker by pepsin digest |
| --- | --- |
| Starting material (T0 control) | 85 |
| 0.5M Arg [pH 7.2, 40° C., t = 1 w] | 63 |
| 20 mM Tris [pH 7.2, 40° C., t = 1 w] | 66 |
| 20 mM Tris, 6% hpβCD, [pH 7.2, 40° C., t = 1 w] | 69 |

Example 4: Cyclodextrin Concentration Profile

This experiment tested the utility of 3 w/v % hydroxypropyl-β-cyclodextrin (hpb-CD), as a component of the diafiltration buffer, to prevent aggregation of a quenched conjugation reaction mixture (QCR) comprising h2H12-1 during diafiltration. A primary goal of this experiment was to determine whether or not the membrane to be used for diafiltration was permeable to hpb-CD. If the membrane were poorly permeable to hpb-CD its concentration in the batch would increase above the concentration in the diafiltration buffer, while if it were readily permeable, the hpb-CD concentration in the batch would reach the concentration in the diafiltration buffer and remain at that level.

The diafiltration (DF) process used an 88 cm$^2$ Ultracel Pellicon 3 cassette from Millipore with a 30 kD molecular weight pore size. The batch volume for the DF was 250 mL, the feed flow rate was 40 ml/min throughout the process, and the retentate valve was adjusted to maintain a trans-membrane pressure of ~20 psi. The diafiltration buffer addition rate to maintain constant batch volume started at 9 mL/min, but was maintained at 13-14 ml/min through most of the process. Samples were removed after the completion of each diavolume. The concentration of hpb-CD was measured in each sample using an RP HPLC assay with evaporative light scattering detection.

Figure 14:
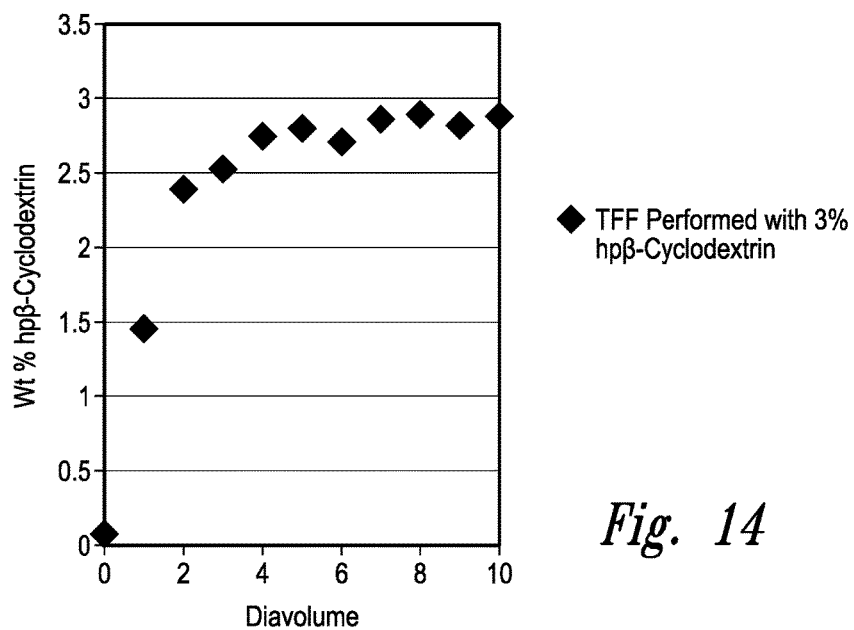
FIG. 14 provides a graph showing the concentration of hydroxypropyl beta cyclodextrin during a diafiltration process. Diafiltration buffer contained 3% w/v cylodextrin. Data shows that membrane is permeable to cyclodextrin.

The results showed the concentration of hpb-CD increasing from 0 at the beginning of the diafiltration to 2.8-2.9 wt % over 5 diavolumes, then remaining constant for an additional 5 diavolumes (FIG. 14). The concentration profile of hpb-CD is consistent with a reagent that is readily permeable to the ultrafiltration membrane used.

Example 5: Tangential Flow Filtration with 3% and 10% w/v Cyclodextrin

In this experiment, a QCR was utilized containing h2H12-1, 50 w/w % propylene glycol, quenched drug-linker (compound 4), and NAC, in 50 mM Tris/5 mM EDTA, pH 8.0. This mixture was brought to 10 w/v % hpb-CD by addition of 25% volume of a 50 w/v % solution of hpb-CD in 50 mM Tris/5 mM EDTA, pH 8.0. The mixture then underwent diafiltration, under conditions similar to Example 4, but scaled appropriately. Samples were removed after each diavolume, and frozen until analysis. The concentration of quenched drug-linker was determined in each sample. The concentration of quenched drug-linker dropped throughout the diafiltration in a manner that follows the established model for clearance through constant volume diafiltration, as shown by a linear relationship between $\ln(C/C_0)$ and diavolume #: $C/C_0 = \exp(-SN)$. C and $C_0$ are concentrations of the analyte measured, N is the number of diavolumes, and S is the sieving factor, defined as the analyte concentration on the permeate side of the membrane divided by the analyte concentration on the retentate side of the membrane. The starting concentration was 16.3 µM, and the final concentration was 0.14 µM.

Figure 15:
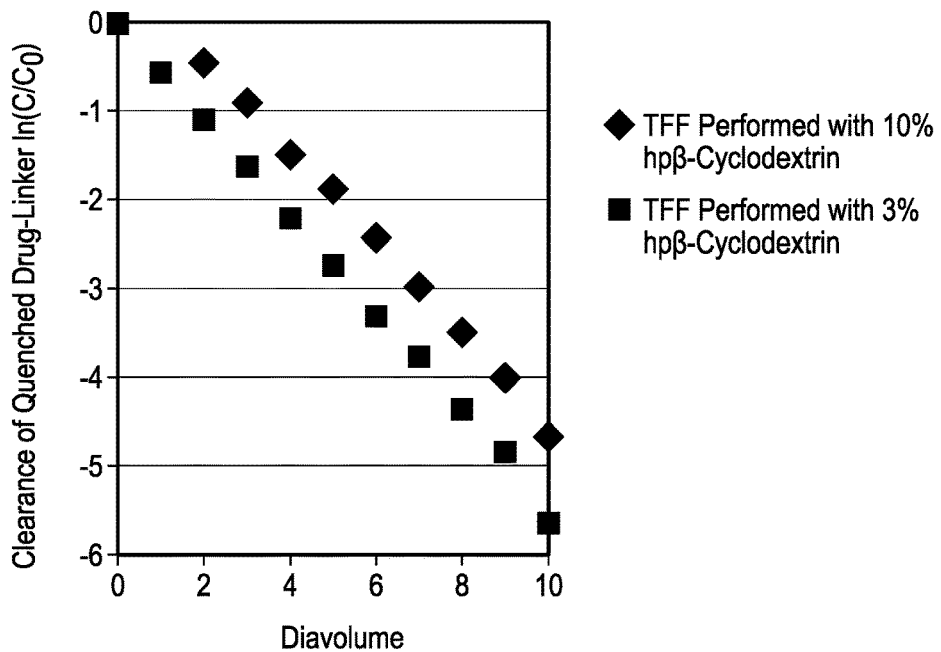
FIG. 15 provides a graph showing the clearance of quenched drug-linker from a quenched conjugation reaction mixture while maintaining a concentration of 10% w/v cyclodextrin (diamonds) or 3% w/v cyclodextrin (squares)

In the presence of 10 w/v % hpb-CD, quenched PBD drug-linker is effectively cleared in this diafiltration process (FIG. 15). Unlike previous experiments in which clearance stopped after a certain number of diavolumes in the absence of hpb-CD, in this experiment clearance was effective to a very low level. The experiment demonstrates that effective and complete clearance can be achieved under the conditions tested.

The experiment was repeated with a lower concentration of hpb-CD (FIG. 15). Essentially identical clearance was observed when 3 w/v % hpb-CD was substituted for 10%.

Example 6: Clearance of Drug-Related Impurities from QCR Mixture

The experiments described in Examples 4 and 5 showed that quenched PBD drug-linker could be removed from a mixture by a diafiltration process using cyclodextrin. The purpose of this experiment was to determine whether this method could successfully clear quenched drug-linker from a QCR having a higher starting concentration of the quenched PBD drug-linker.

Stored frozen reduced antibody (h2H12 reduced as to 239 position but not as to interchain disulfides) was thawed. Propylene glycol (PG), followed by drug-linker-PG/DMA (compound 1), was added to form the conjugation reaction mixture. The mixture contained 50% (v/v) PG, and excess drug-linker (compound 4). The reaction proceeded about 90 min, after which 3.0 equivalents (relative to drug-linker) NAC were added, and the quench reaction was allowed to proceed about 30 min.

Sufficient 50 w/w % hpb-CD stock solution was added to bring the quenched conjugation reaction hpb-CD concentration to 3%. The TFF process was started, by turning on the TFF feed pump, using an 88 cm2 regenerated cellulose membrane. As with previous TFF processes of solutions containing high percentages of PG, the initial flow rate was limited due to high trans-membrane pressure, but during the first diavolume the feed flow rate could be gradually increased into the recommended operating range for the membrane. Thereafter, the retentate valve was adjusted to maintain the TMP of 20 psi. Diafiltration buffer was added to maintain constant volume. The process was allowed to continue for 20 diavolumes, and samples were taken after each diavolume and frozen for subsequent analysis.

Figure 16:
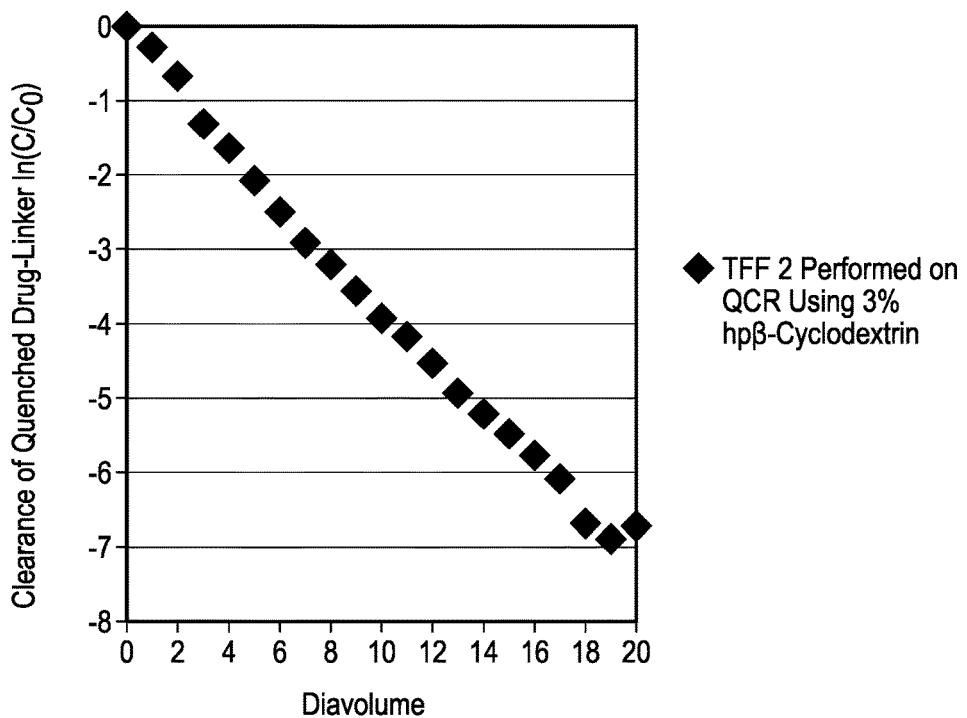
FIG. 16 provides a graph showing the clearance of quenched drug-linker from a quenched conjugation reaction mixture while maintaining a concentration of 3% w/v cyclodextrin.

Measurement of the concentration of quenched PBD drug-linker (compound 4) in the solution in samples taken throughout the purification process showed that the material was cleared by the TFF process. The concentration started at 27.47 µM and dropped to 0.03 µM after 20 diavolumes, showing that quenched PBD drug-linker could be cleared by TFF from a QCR solution (FIG. 16). Analysis of the final product sample showed that average drug load and distribution, disulfide bond integrity, charge distribution, and UV spectrum, were not adversely affected by this process (data not shown).

Example 7: Clearance of Drug-Related Impurities from QCR Mixture Comprising 2H12 ADCs or h1F6 ADCs The TFF process was performed on quenched conjugation reaction mixture using a 30 kD MW cutoff 0.1 m$^2$ Ultracel Pellicon 3 membrane (Millipore). The TMP was maintained at 20 psi, initially maintained by flow rate, then by retentate valve. The TFF process ran for 20 diavolumes, with samples collected every $2^{nd}$ diavolume. The concentration of quenched PBD drug-linker was determined in each sample.

Figure 17:
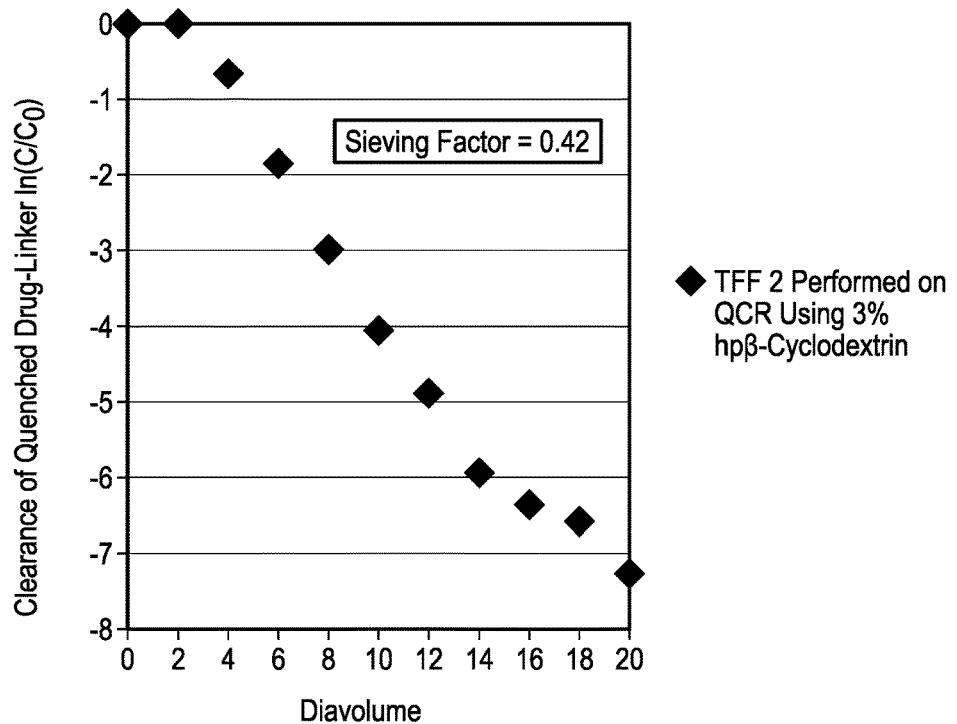
FIG. 17 provides a graph showing the clearance of quenched drug-linker from a quenched conjugation reaction mixture while maintaining a concentration of 3% w/v cyclodextrin.

In one experiment with a QCR mixture comprising 2H12 ADCs, the concentration of quenched PBD drug-linker (compound 4) dropped from 29.56 mM to 0.02 mM during the TFF process. The clearance plot was linear, with a sieving factor of ~0.4. Data on recovery during the TFF step is not available, but overall yield for the ADC was >95%, so loss during the TFF process was <5% (FIG. 17)

TFF is as effective as carbon-filtration for clearance of quenched PBD drug-linker, in the presence of 3% hpb-CD. Based on examination of the drug-related impurities during the TFF process, it is estimated that 14 diavolumes is sufficient to assure achieve a sufficiently low impurity level.

Figure 18:
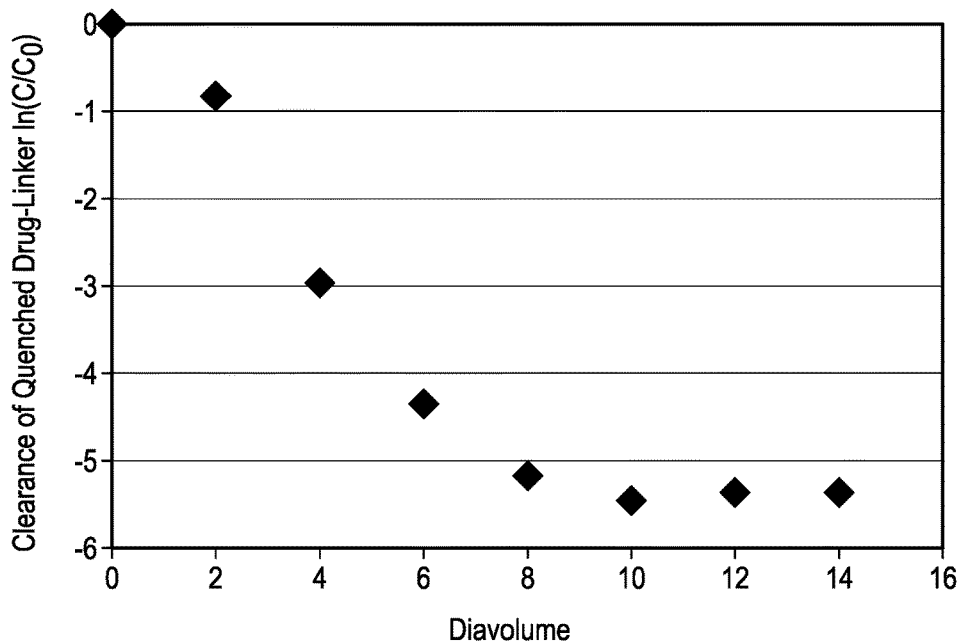
FIG. 18 provides a graph showing the clearance of quenched drug-linker from a quenched conjugation reaction mixture while maintaining a concentration of 3% w/v cyclodextrin.

In one experiment with a QCR mixture comprising h1F6 ADCs, the concentration of quenched PBD drug-linker (compound 4) dropped from 21.2 mM to 0.1 uM during the TFF process. The clearance plot was linear, with a sieving factor of ~0.6. (FIG. 18)z

Example 8: Purification of Benzodiazepine ADCs Using Tangential Flow Filtration without Cyclodextrin Quenched drug-linker (compound 4) was purified from the QCR using constant volume diafiltration. The quenched conjugation reaction mixture was introduced into the tangential flow filtration device. The quenched conjugation reaction mixture comprises Tris, NaCl and 50% propylene glycol. The tangential flow filtration buffer also comprises Tris, NaCl and 50% propylene glycol. After the ultrafiltration/diafiltration sequence, 1.1 uM benzodiazepine drug-related impurity remained in the mixture with the clearance stalling after four diavolumes. (data not shown)

Example 9: Cytotoxicity

Cytotoxicity studies were performed to determine whether ADC formulations containing 6% cyclodextrin retained cytotoxic activity. The results demonstrated that the ADC formulations retained cytotoxic activity (data not shown).

Example 10: Clearance of Drug-Related Impurities from Unquenched Conjugation Reaction Mixture Unquenched PBD drug-linker having a S log P value of 7.57 (compound 1) was purified from an unquenched conjugation reaction mixture using constant volume diafiltration. Cyclodextrin was maintained at 3%. Surprisingly, clearance of the unquenched PBD linker (data not shown) was not as efficient as clearance of the quenched PBD drug-linker as shown in the previous examples. This experiment demonstrated that lowering the hydrophobicity of the PBD drug-linker (compound 4 has a S log P value of 5.76) improved clearance.

What is claimed is:

1. A pharmaceutically acceptable formulation comprised of (a) benzodiazepine ADC having the structure of:

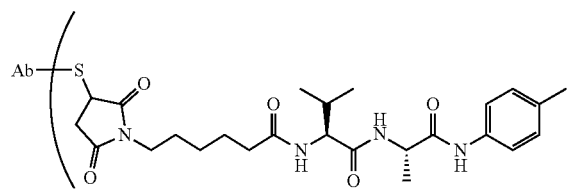

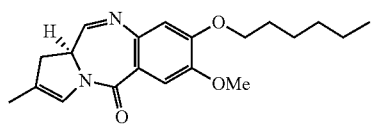

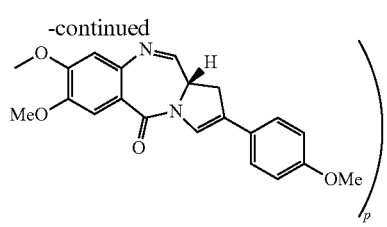

or a pharmaceutically acceptable salt thereof, wherein

Ab is a monoclonal antibody that specifically to an extracellular domain of human CD33, wherein the monoclonal antibody is h2H16ec having a variable light chain sequence comprising the amino acid sequence set forth in SEQ ID NO: 3 and a variable heavy chain sequence comprising the amino acid sequence set forth in SEQ ID NO:4 engineered to have introduced cyteine residues at position 239 (EU index numbering);

S represents the sulfur atoms from the engineered cysteine residue;

subscript p, which represents the average number of conjugated drug-linker molecules per monoclonal antibody in the formulation, is about 2, wherein conjugation of the drug-linker molecules is to the sulfur atoms of the introduced cyteine residues; and wherein the concentration of the benzodiazepine ADC ranges from 1.3 mg/mL to 3.1 mg/mL;

(b) no more that 0.1 µM of a benzodiazepine-related impurity having the structure of:

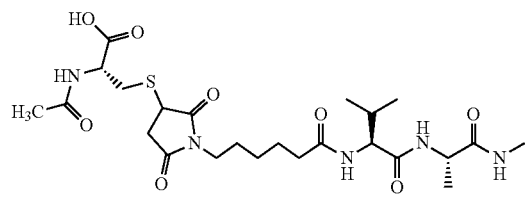

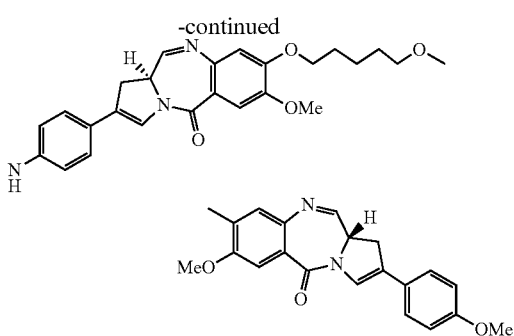

or a pharmaceutically acceptable salt thereof (c) 6% w/v of a chemically modified cyclodextrin, wherein the chemically modified cyclodextrin is hydroxypropyl-β-cyclodextrin;

(d) a lyoprotectant, wherein the lyoproptectant is 6% w/v sucrose; and (e) a diluent, wherein the diluent is 20 mM KPhos buffer at a pH of 7.3.

* * * * *

UNITED STATES PATENT AND TRADEMARK OFFICE
CERTIFICATE OF CORRECTION

PATENT NO. : 10,391,181 B2
APPLICATION NO. : 15/967276
DATED : August 27, 2019
INVENTOR(S) : Hui Li et al.

It is certified that error appears in the above-identified patent and that said Letters Patent is hereby corrected as shown below:

In the Claims

In Claim 1, the structure at Column 61, Line 51, to Column 62, Line 54, is replaced with the following structure:

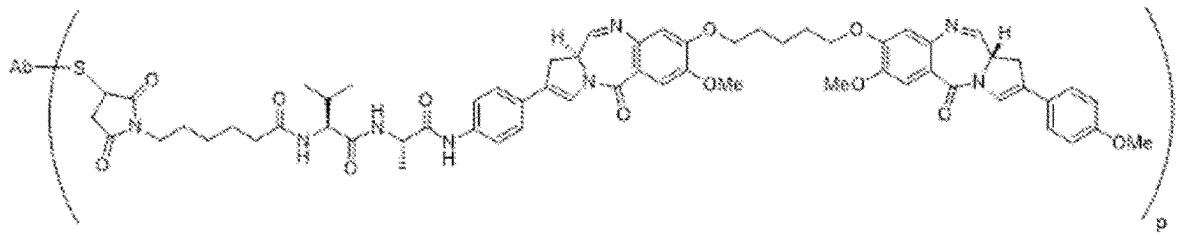

In Claim 1, the structure at Column 63, Line 14, to Column 64, Line 14, is replaced with the following structure:

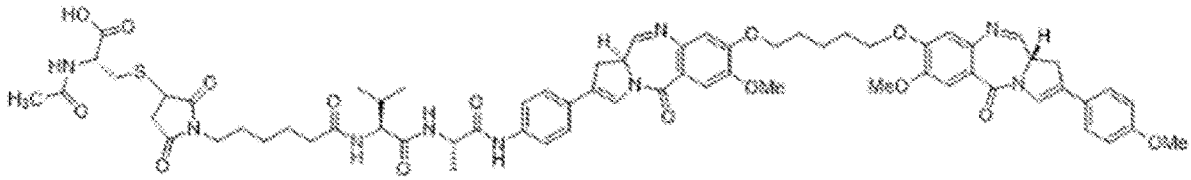

Signed and Sealed this
Twenty-seventh Day of October, 2020

Andrei Iancu
*Director of the United States Patent and Trademark Office*